(12) United States Patent
Assell et al.

(10) Patent No.: US 11,337,710 B2
(45) Date of Patent: May 24, 2022

(54) BONE FRAGMENT AND TISSUE HARVESTING SYSTEM

(71) Applicants: Fortus Medical, Inc., Minneapolis, MN (US); The Cleveland Clinic Foundation, Cleveland, OH (US)

(72) Inventors: Robert Assell, Minneapolis, MN (US); Andy Freeman, Minneapolis, MN (US); George Muschler, Minneapolis, MN (US)

(73) Assignees: Fortus Medical, Inc., Minneapolis, MN (US); The Cleveland Clinic Foundation, Cleveland, OH (US)

( * ) Notice: Subject to any disclaimer, the term of this patent is extended or adjusted under 35 U.S.C. 154(b) by 272 days.

(21) Appl. No.: 16/808,987

(22) Filed: Mar. 4, 2020

(65) Prior Publication Data
US 2020/0197024 A1 Jun. 25, 2020

Related U.S. Application Data

(63) Continuation of application No. 15/150,121, filed on May 9, 2016, now Pat. No. 10,610,242.
(Continued)

(51) Int. Cl.
*A61B 17/16* (2006.01)
*A61B 17/88* (2006.01)
(Continued)

(52) U.S. Cl.
CPC ...... *A61B 17/1615* (2013.01); *A61B 17/1635* (2013.01); *A61B 17/8805* (2013.01);
(Continued)

(58) Field of Classification Search
CPC ............ A61B 17/1615; A61B 17/1635; A61B 17/8805; A61B 17/8811; A61B 17/8833;
(Continued)

(56) References Cited

U.S. PATENT DOCUMENTS

| 4,969,870 A | 11/1990 | Kramer |
| 5,152,763 A | 10/1992 | Johnson |

(Continued)

FOREIGN PATENT DOCUMENTS

| DE | 19949866 A1 | 11/2001 |
| WO | 1999/59500 A2 | 11/1999 |

OTHER PUBLICATIONS

International Search Report and Written Opinion received for PCT Serial No. PCT/US2021/018570 dated May 7, 2021, 9 pgs.
(Continued)

*Primary Examiner* — Samuel S Hanna
(74) *Attorney, Agent, or Firm* — Michael A. Bondi; Moss & Barnett

(57) ABSTRACT

A bone fragment and osteomedullary tissue harvesting system that includes a harvesting device, a collection vessel and tubing. The harvesting device includes a needle portion and a handle portion. The needle portion that has a needle bore that extends through at least part of the needle portion. The handle portion is operably attached to the needle portion. The handle portion includes a connection port and a vacuum control mechanism that are in communication with a handle bore that extends through the handle portion. The needle bore is in communication with the handle bore. The vacuum control mechanism includes a vacuum aperture that extends through a surface of the handle portion and is in communication with the handle bore. The collection vessel is capable of receiving aspirated bone fragments and tissue. The tubing operably connects the connection port and the collection vessel.

6 Claims, 10 Drawing Sheets

Related U.S. Application Data

(60) Provisional application No. 62/193,451, filed on Jul. 16, 2015, provisional application No. 62/158,574, filed on May 8, 2015.

(51) Int. Cl.
  *A61J 1/14* (2006.01)
  *C12M 1/26* (2006.01)
  *C12M 1/33* (2006.01)
  *A61M 1/00* (2006.01)
  *A61J 1/20* (2006.01)
  *A61L 27/36* (2006.01)
  *A61L 27/38* (2006.01)
  *A61B 17/00* (2006.01)

(52) U.S. Cl.
  CPC ...... *A61B 17/8811* (2013.01); *A61B 17/8833* (2013.01); *A61J 1/1475* (2013.01); *A61J 1/1481* (2015.05); *A61J 1/1487* (2015.05); *A61J 1/2058* (2015.05); *A61J 1/2086* (2015.05); *A61L 27/3608* (2013.01); *A61L 27/3687* (2013.01); *A61L 27/3691* (2013.01); *A61L 27/3834* (2013.01); *A61M 1/79* (2021.05); *C12M 33/04* (2013.01); *C12M 33/14* (2013.01); *C12M 45/02* (2013.01); *A61B 2017/00561* (2013.01); *A61J 2200/76* (2013.01); *A61L 2430/02* (2013.01)

(58) Field of Classification Search
  CPC .... A61B 2017/00561; A61B 2217/005; A61B 10/025; A61B 2010/0258
  See application file for complete search history.

(56) References Cited

U.S. PATENT DOCUMENTS

| | | |
|---|---|---|
| 5,269,785 A | 12/1993 | Bonutti |
| 5,456,267 A | 10/1995 | Stark |
| 5,807,353 A | 9/1998 | Schmitz |
| 5,824,084 A | 10/1998 | Muschler |
| 6,022,354 A | 2/2000 | Mercuri |
| 6,049,026 A | 4/2000 | Muschler |
| 6,132,448 A | 10/2000 | Perez |
| 6,406,454 B1 | 6/2002 | Hajianpour |
| 6,673,629 B2 | 1/2004 | Yoshimura |
| 6,723,131 B2 | 4/2004 | Muschler |
| 6,981,948 B2 | 1/2006 | Pellegrino |
| 8,109,919 B2 | 2/2012 | Kraft |
| 8,137,408 B2 | 3/2012 | Kadiyala |
| 8,343,133 B2 | 1/2013 | Allee |
| 8,439,929 B1 | 5/2013 | Sharratt |
| 8,579,912 B2 | 11/2013 | Isaza |
| 8,852,119 B2 | 10/2014 | Wawrzyniak |
| 2002/0058945 A1 | 5/2002 | Steiner |
| 2002/0082519 A1 | 6/2002 | Miller |
| 2002/0161449 A1 | 10/2002 | Muschler |
| 2003/0031695 A1 | 2/2003 | Kadiyala |
| 2004/0071668 A1 | 4/2004 | Barry |
| 2005/0101963 A1 | 5/2005 | Merboth |
| 2005/0130301 A1 | 6/2005 | McKay |
| 2006/0246150 A1 | 11/2006 | Thorne |
| 2006/0264964 A1 | 11/2006 | Scifert |
| 2007/0055282 A1 | 3/2007 | Muschler |
| 2007/0198043 A1 | 8/2007 | Cox |
| 2008/0103605 A1 | 5/2008 | Kadiyala |
| 2008/0145392 A1 | 6/2008 | Knaack |
| 2008/0195115 A1 | 8/2008 | Oren |
| 2008/0288006 A1 | 11/2008 | Brannon |
| 2009/0014391 A1 | 1/2009 | Leach |
| 2009/0081689 A1 | 3/2009 | Yamanishi |
| 2009/0137927 A1 | 5/2009 | Miller |
| 2009/0187116 A1 | 7/2009 | Noishiki |
| 2009/0287190 A1 | 11/2009 | Shippert |
| 2011/0257557 A1 | 10/2011 | Pesce |
| 2012/0116247 A1* | 5/2012 | Wawrzyniak ........ A61B 10/025 600/567 |
| 2013/0030547 A1 | 1/2013 | Burkinshaw |
| 2013/0131545 A1 | 5/2013 | Azimpoor |
| 2014/0100574 A1 | 4/2014 | Bono |
| 2014/0105960 A1 | 4/2014 | Zoldan |
| 2014/0257133 A1 | 9/2014 | Landrigan |
| 2014/0274894 A1 | 9/2014 | Leach |
| 2014/0363403 A1 | 12/2014 | Segina |
| 2015/0110890 A1 | 4/2015 | Assell |
| 2015/0164949 A1 | 6/2015 | Sowemimo-Coker |
| 2015/0182268 A1 | 7/2015 | Donner |
| 2016/0325018 A1 | 11/2016 | Assell |
| 2016/0331878 A1 | 11/2016 | McGillicuddy |
| 2018/0353206 A1 | 12/2018 | Assell |

OTHER PUBLICATIONS

McLain, et al. "Transpedicular aspiration of osteoprogenitor cells from the vertebral body: progenitor cell concentration affected by serial aspiration", The Spine Journal, Oct. 19, 2009, vol. 9, No. 12, pp. 995-1002.

Duguy N., et al.: "Biomaterials and osseous regeneration", Annales De Chirurgie Plastique Esthetique, Expansion Scientifique Francaise, Paris, France, vol. 45, No. 3, Jun. 1, 2000, pp. 364-376, Issn: 0294-1260.

Ripamonti U., et al., "Tissue Engineering of Bone by Osteoinductive Biomaterials", MRS Bulletin, Pittsburgh, US, vol. 21, No. 11, Nov. 1, 1996, XP008005014, pp. 36-39.

Kurita, et al., "Differential Effects of Three Preparations of Human Serum on Expansion of Various Types of Human Cells", American Society of Plastic Surgeons, Dec. 20, 2007, 12 pgs.

* cited by examiner

Fig. 3
Prior Art
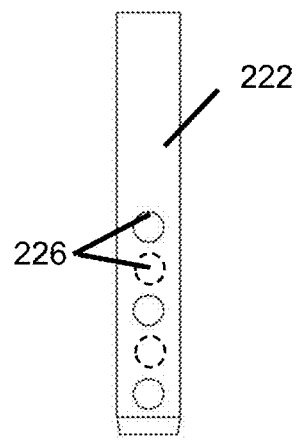
Fig. 5
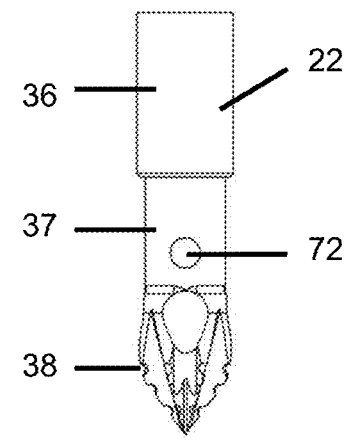
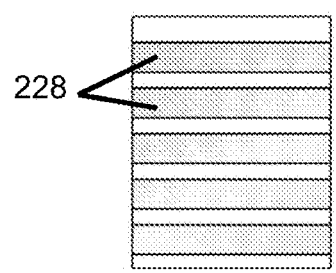
Fig. 4
Prior Art
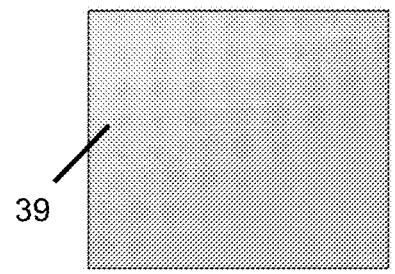
Fig. 6

BONE FRAGMENT AND TISSUE HARVESTING SYSTEM

REFERENCE TO RELATED APPLICATION

This application is a continuation of U.S. application Ser. No. 15/150,121, filed on May 9, 2016; which claims priority to U.S. Provisional Applic. No. 62/158,574, filed on May 8, 2015, and U.S. Provisional Applic. No. 62/193,451, filed on Jul. 16, 2015, the contents of which are incorporated herein by reference.

FIELD OF THE INVENTION

The invention relates generally to harvesting of bone fragments and tissue. More particularly, the invention relates to a bone fragment and tissue harvesting system.

BACKGROUND OF THE INVENTION

Traditionally, doctors have used a large bore needle to aspirate bone fragments and/or marrow. However, orthopedic companies have developed their own versions of bone marrow aspirate concentrate systems for use specifically with bone graft substitute. These disposable kits are used for aspirating and concentrating the stem cells found in the bone marrow onto a graft matrix to be implanted into the patient. Combined with a bone graft substitute, bone marrow aspirate concentrate may provide similar results to an autograft (Geistlich, 2011).

An example of one such prior art bone marrow aspiration needle is disclosed in Allee et al., U.S. Pat. No. 8,343,133. This device includes a handle and a needle that extends therefrom. The needle has a central bore that in addition to facilitating the aspiration of the bone marrow also enables a guide wire to extend therethrough to facilitate accurate placement of the device in bone. The handle includes a port to which a syringe is attached to cause the bone marrow to be aspirated through the needle.

Landrigan et al., U.S. Patent Publication No. 2014/0257133, discloses a bone marrow aspiration needle that is fabricated from a flexible material. Landrigan indicates that the cannulated introducer needle can be curved to approximate the natural curvature of the iliac crest.

Wawrzyniak et al., U.S. Pat. No. 8,852,119, describes a flexible bone marrow aspiration needle having a helical groove in an outer surface thereof. An elastomeric overcoat covers at least a portion of the groove.

In the US, bone grafts are most commonly used in spine fusion surgery and, more generally, in the fusion or arthrodesis of any skeletal joint. In addition, bone graft is generally used in trauma surgery for the treatment of fresh fractures and non-unions, which are typically identified as fractures within 6 months that have not healed properly. The bone graft materials typically bridge a gap between bone segments and may also provide a three-dimensional scaffold on which the bone can grow.

Bone graft treatment is also typically used in conjunction with fresh fractures where the bone has been shattered or where the patient is at a very high risk of developing a non-union fracture. Because many fractures are not this severe and can be treated with alternative methods of fixation, bone grafts are not frequently needed during fresh fracture treatments.

Two areas where bone grafts are used is in conjunction with joint reconstruction and joint revision. For example, the bone graft may be used to fill a void between the bone and joint implant in a joint reconstruction surgery. Joint revision is much more likely to need a bone graft because a large void may result from the removal of the original implant. Joint revisions that use bone graft material therefore usually require a relatively large quantity of the bone graft material.

There are different types of bone graft materials that may be used to assist a patient's body in bone regeneration. These bone graft materials are typically classified as either natural or synthetic materials.

Natural bone graft materials are classified in the following groups. Autograft is bone graft material that is obtained from the same individual that will receive the bone graft material. Allograft is bone graft material that is obtained from another human source, which typically is from cadavers. Xenograft is bone graft material that is obtained from another species.

Bone grafts can also be categorized by their bone-forming properties as osteoconductive, osteoinductive or osteogenic. Osteoconductivity is the ability of a material to provide an appropriate scaffold or matrix upon which new bone tissue can form. Osteoinductivity is the ability of a material to stimulate the patient's own system to form new bone. Osteogenic material generates new bone tissue itself. Osteoblasts, which can be found in bone marrow and mesenchymal cells, are the only cells that can create new bone.

Autograft bone has historically been the standard of care because of its osteoconductive, osteoinductive and osteogenic properties. At the time of surgery bone is taken from a donor site in the patient, often the iliac crest bone but others are used, and then is re-implanted back into the patient at the surgical site.

Autograft is often not used, because obtaining the graft generally requires a second surgical procedure with associated risks and expenses. The autograft also typically results in significant post-operative issues, most significantly pain. An additional type of autograft, concentrated cells from bodily fluids such as blood or bone marrow, is often used as well.

In addition to autograft, many other types of bone graft are used including processed cadaver bone, i.e., allograft, in the form of demineralized bone matrix and also so called "living cell" or "stem cell" allograft. Additionally, constituents know to be involved in new bone formation, such as bone morphogenic proteins, typically produced by recombinant processing means, as used. Synthetic materials such as tri-calcium phosphate, calcium sulphate, hydroxyapatite and others are used as well.

Summary of Bone Graft Characteristics by Material

| Type | Osteoconductive | Osteoinductive | Osteogenic |
| --- | --- | --- | --- |
| Autograft | Yes | Yes | Yes |
| Bone morphogenic proteins | No | Yes (strong) | Yes |
| Demineralized bone matrix | Yes | Minimal | No |
| Allogeneic stem cell | Yes | Unknown | Yes |
| Bone marrow aspirate | Yes | Yes (strong) | Yes |
| Synthetics | Yes | No | No |

Bone graft substitutes also fall within the classification of bone filler materials. Examples of bone graft substitutes include collagen, polymers such as silicone and some acrylics, hydroxyapatite, calcium sulfate and ceramics.

Bone cement (such as polymethylmethacylate) can be used as a bone void filler to treat bone voids or defects. For example, it can be used to repair fractured bones and vertebral bodies. The bone cement can be used either in procedures that involve direct injection of the bone cement into the fractured vertebral body (i.e., vertebroplasty) or injection of the bone cement into the vertebral body after the height of the vertebral body is restored using a pressurized balloon (i.e., kyphoplasty).

One of the disadvantages of using bone cement is that, once it is injected inside the patient, the bone cement is an inorganic material and, as such, is treated as a foreign body. As such, the bone cement may not only negatively impact healing but can also lead to bone disease.

Additionally, the bone cement is typically stiffer than bone, which may increase the incidence of adjacent level fractures in the spine. Bone cement leakage may cause complications, and has been reported to occur in vertebroplasty and kyphoplasty procedures. If leakage does occur, the bone cement can cause soft tissue injury due to the high temperatures of the exothermic polymerization reaction. In addition, if the bone cement is forced into the vascular system, it can cause emboli.

Bone marrow and bone marrow aspirate concentrate are considered to have a significantly higher bioactivity than circulating blood or concentrated blood known as platelet rich plasma. These features mean that bone marrow is often viewed as being superior to platelet rich plasma for use in orthopedic applications such as spinal fusion and trauma surgery because the bone marrow contains progenitor cells and multipotent stem cells, which assist in the formation of new bone.

Bone marrow aspirate concentrate has become increasingly popular in bone growth applications, particularly spinal fusion and trauma surgery, because of its osteogenic properties. Traditionally, autograft was the gold standard grafting material in these procedures due to the presence of osteoblasts and osteogenic precursor cells, as well as its osteoconductive and osteoinductive properties.

To avoid the risks associated with autograft procurement such as donor site infection and morbidity, bone marrow aspirate concentrate has been increasingly used because it has similar properties as autograft and allows surgeons and patients to avoid autograft procurement.

One system for aspirating bone marrow is disclosed in Pellegrino et al., U.S. Pat. No. 6,981,948. One configuration of the bone marrow aspiration system includes a needle that extends generally transverse from a handle. A vacuum line is connected to the handle to cause bone marrow to be drawn through the needle and into the handle.

Cox et al., U.S. Patent Publication No. 2007/0198043, discloses the use of a curved bone marrow aspiration needle. Cox indicates that the curved bone marrow aspiration needle enables bone marrow to be aspirated from different areas by changing a distance that the bone marrow aspiration needle is inserted and by rotating the bone marrow aspiration needle.

SUMMARY OF THE INVENTION

An embodiment of the invention is directed to a method of harvesting bone fragments and osteomedullary tissue. A harvesting device is provided that includes a needle portion and a tip portion. The needle portion has a bore formed therein. The tip portion extends from an end of the needle portion. An aperture is formed in a bone. At least part of the needle portion is inserted through the aperture into the bone. The harvesting device rotated to cause the bone fragments to be formed and tissue to be morselized. A vacuum is applied to a proximal end of the bore to cause the bone fragments and morselized tissue to be aspirated from the bone.

Another embodiment of the invention is directed to a bone fragment and osteomedullary tissue harvesting system that includes a harvesting device, a collection vessel and tubing. The harvesting device includes a needle portion and a handle portion. The needle portion has a needle bore that extends through at least part of the needle portion. The handle portion is operably attached to the needle portion. The handle portion includes a connection port and a vacuum control mechanism that are in communication with a handle bore that extends through the handle portion. The needle bore is in communication with the handle bore. The vacuum control mechanism has a vacuum aperture that extends through a surface of the handle portion and is in communication with the handle bore. The collection vessel is capable of receiving aspirated bone fragments and tissue. The tubing operably connects the connection port and the collection vessel.

Another embodiment of the invention is directed to a bone fragment and tissue osteomedullary harvesting needle that includes a needle portion and a tip portion. The needle portion has a bore formed therein. The tip portion extends from an end of the needle portion and includes a first tip region, a second tip region and a third tip region. The first tip region has at least one cutting surface and a recessed region proximate the at least one cutting surface. The first tip region has an outer diameter. The second tip region has an outer diameter that is less than the outer diameter of the first tip region. The recessed region is in communication with the second tip region. The second tip region has at least one aperture formed therein. The at least one aperture is in communication with the bore. The third tip region has an outer diameter that is not smaller than the outer diameter of the first tip region. The second tip region is intermediate the first tip region and the third tip region. The third tip region is proximate the main needle portion.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

FIG. 3 is a side view of a prior art bone marrow aspiration needle.

FIG. 4 is an illustration of an aspiration area provided by the bone marrow aspiration needle of FIG. 3.

FIG. 5 is a side view of the needle of FIG. 2.

FIG. 6 is an illustration of an aspiration area provided by the needle of FIG. 5.

DETAILED DESCRIPTION OF THE INVENTION

Figure 1:
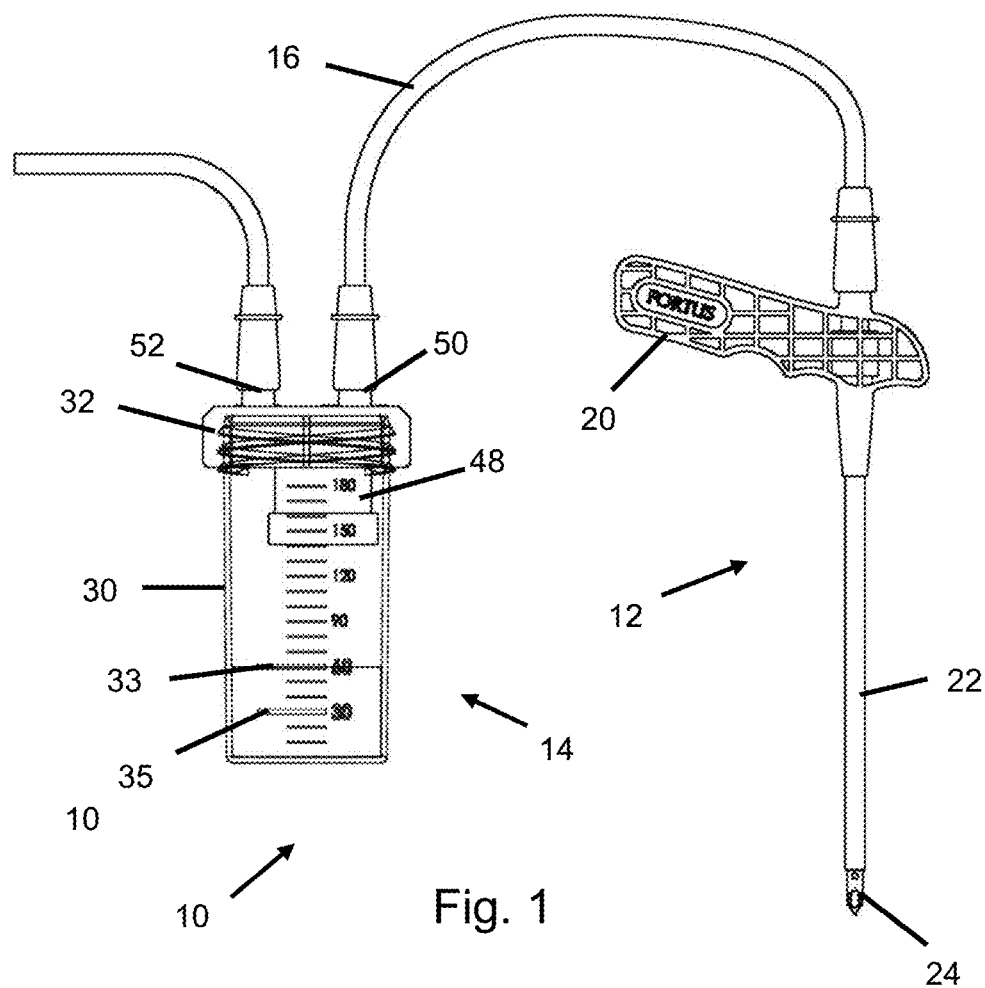
FIG. 1 is a side view of a bone fragment and tissue harvesting and processing system according to an embodiment of the invention.

An embodiment of the invention is directed to a bone fragment and tissue harvesting and processing system, which is illustrated in FIG. 1. The bone fragment and tissue harvesting and processing system 10 generally includes a harvesting device 12 that is operably attached to a processing device 14 with tubing 16.

The bone fragment and tissue harvesting and processing system 10 facilitates extraction of bone fragments and tissue from a patient that are then used in preparing a bone graft, as is described in more detail herein.

The terms bone fragments and tissue, as used herein, are intended to be broadly construed to encompass all aspiratable components within the bone regardless of the nature of such components.

A significant advantage of the invention is that it is a contained system, which facilitates use of the invention in an operating room as well as in an out-patient setting. The invention thereby enables high-quality bone grafts to be prepared in a cost-effect manner proximate to when it is desired to use the bone graft.

The invention thereby provides a completely autologous process that enables use of the patient's own tissue in preparing a bone graft. In addition to harvesting bone fragments, the invention enables high yield harvesting of stem and progenitor cells as well as collection of intramedullary bone graft in a process that is safe, fast and efficient. This tissue is used in conjunction with an osteoconductive matrix to form a bone graft.

The harvesting device 12 includes a handle portion 20 and a needle portion 22 that are operably connected to each other. In certain embodiments, the needle portion 22 is detachably connected to the handle portion 20. In other embodiments, the needle portion 22 is integrally formed with the handle portion 20.

In certain embodiments, the needle portion 22 may have an outer diameter of about 6 millimeters. Forming the needle portion with this diameter minimizes the potential that bone fragments will become stuck while being drawn through the needle portion 22 during the aspiration process.

The needle portion 22 having the preceding characteristics may have a two-part configuration that include an inner shaft and an outer shaft. The inner shaft may be fabricated from a metallic material such as stainless steel. The metallic material thereby provides the needle portion 22 with a relatively high strength while having a relatively thin wall thickness. In certain embodiments, the wall thickness of the metallic material may be less than about 10 thousandths of an inch. In certain embodiments, the wall thickness of the inner shaft is between about 3 and 6 thousandths of an inch. In still other embodiments, the wall thickness of the inner shaft is about 4 thousandths of an inch.

Fabricating the inner shaft with a relatively thin wall thickness allows the inner channel to be relatively wide to facilitate a large flow rate of bone fragments and tissue therethrough while at the same time having a relatively small outer diameter to minimize the size of the hole that is formed in the bone to access the interior of the bone where the bone fragments are formed and the beneficial tissue is located.

The outer shaft may be fabricated from a polymeric material that is molded over the inner shaft. The outer shaft thereby enhances strength of the inner shaft while allowing the needle to deflect during the bone marrow and tissue harvesting process. The combined structure of the inner shaft and the outer shaft provides the needle portion 22 with enhanced torsional strength compared to a needle fabricated only from a metallic material or a polymeric material.

Another advantage of using the polymeric outer shaft over the metallic inner shaft is that it is possible for the bore that extends through the inner shaft to have a relatively constant size over the length of the needle portion 22. If the needle portion 22 had been fabricated only from a polymeric material, it would have been necessary for the inner diameter to taper when moving from the proximal end to the distal end of the needle portion 22 to facilitate molding of the needle portion 22.

Because of the length of the needle portion 22, such tapering would have resulted in a relatively thick wall proximate the proximal end, a relatively thin wall proximate the distal end or combination thereof. Such differences in wall thickness would have limited the flexing of the needle portion 22 near the proximal end while providing too much flexibility proximate the distal end. Both of these situations would have limited the ability to maneuver the needle during the bone fragment and tissue recovery process.

An outer diameter of the needle portion 22 may be wider proximate the handle portion 20. Using such a configuration increases the strength of the harvesting device 12 such that there is less likelihood of the harvesting device 12 deforming during the process of forming the bone fragments, morselizing the tissue inside of the bone or when aspirating the bone fragments and tissue from the bone.

To provide the needle portion 22 with a desired level of sharpness, the needle portion 22 has a tip that is fabricated from a metallic material as the metallic material provides an enhanced sharpness as compared to a tip 24 fabricated from a polymeric material. The tip 24 may be attached to the distal end of the inner tube before the outer tube is molded over the inner tube.

Figure 2:
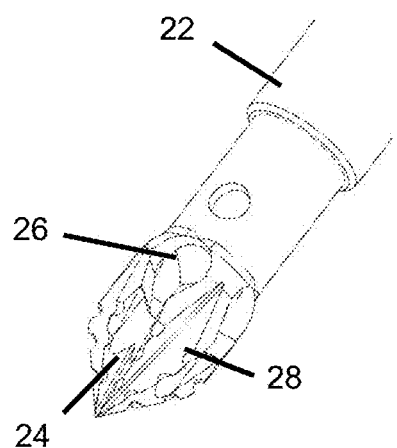
FIG. 2 is a perspective view of a needle for use in conjunction with the bone fragment and tissue harvesting and processing system of FIG. 1.

The sharpened tip 24, which is most clearly illustrated in FIG. 2, that facilitates accessing the interior of a bone. The sharpened tip 24 also facilitates forming bone fragments. The harvesting device 12 also facilitates morselizing tissue inside of the bone and thereby enhances the amount of osteomedullary tissue that can be recovered from a patient. The bone fragments and tissue are aspirated from the patient using the harvesting device 12, which causes the aspirated tissue to be collected in the processing device 14.

Because there are a relatively large concentration of bone fragments that are aspirated through the harvesting device 12, the tip 24 of the needle portion 22 includes a plurality of relatively large apertures 26 formed therein proximate the distal end thereof. Intermediate the apertures 26 is at least one sharpened surface 28. The at least one sharpened surface 28 facilitates cutting while the needle portion 22 is inserted into and removed from the bone. The at least one sharpened surface 28 also facilitates cutting while the needle portion 22 is axially rotated and/or pivoted.

The processing device 14 generally includes a collection vessel 30 to which a collection vessel cap 32 is operably attached. The collection vessel 30 may be formed with a size based upon the volume of bone fragments and tissue that is anticipated to be aspirated from the patient. In certain embodiments, the collection vessel 30 has a volume of about 180 cubic centimeters.

The collection vessel 30 may have a variety of shapes using the concepts of the invention. In certain embodiments, the collection vessel 30 has a generally cylindrical shape. Using such a shape enables the collection vessel cap 32 to be attached using a rotational motion.

A side of the collection vessel 30 may include at least two volume collected markers 33, 35. In one embodiment, the volume collected markers include an upper marker 33 and a lower marker 35. The upper marker 33 and the lower marker 35 thereby provide guidance to the person using the invention regarding whether a desired volume of tissue has been collected. In other embodiments, the volume collected markers may include a series of identifiers that correspond to a conventional volume measuring system such as milliliters.

Proximate an upper end of the collection vessel 30, an opening may be provided. In one such embodiment, the opening is generally circular and has a thread on a surface thereof that can be used when attaching the collection vessel cap 32 to the collection vessel 30. In certain embodiments, the thread may be on an outer surface of the opening. A person of skill in the art will appreciate that a variety of other techniques may be used to attach the collection vessel cap 32 to the collection vessel 30.

One aspect of the attachment of the collection vessel cap 32 to the collection vessel 30 is that a substantially air-tight seal is formed when the collection vessel cap 32 is attached to the collection vessel 30 so that a vacuum may be used to draw the aspirated bone fragments and tissue into the collection vessel 30.

The collection vessel 30 may be fabricated from a variety of materials using the concepts of the invention. In one embodiment, at least a portion of the collection vessel 30 is fabricated from a transparent material. Such a configuration enables a person using the bone fragment and tissue harvesting and processing system 10 to not only view the volume of aspirated tissue in the collection vessel 30 but also other characteristics of the aspirated tissue such as a color of the aspirated tissue and/or the presence of discrete regions in the aspirated tissue.

Another criterion for the material that is used in fabricating the collection vessel 30 is that the material be biologically compatible and facilitate sterilization of the collection vessel 30 prior to use. An example of one such material that may be used to fabricate the collection vessel 30 is polyethylene terephthalate.

The collection vessel cap 32 may have a generally cylindrical configuration with an inner diameter that is selected based upon an outer diameter of the collection vessel 30 proximate the threaded region to facilitate removable attachment of the collection vessel cap 32 to the collection vessel 30. In this regard, the collection vessel cap 32 may include a thread on an inner surface thereof that is shaped generally complementary to the thread on the collection vessel 30.

While not illustrated, at least a portion of the outer surface of the collection vessel cap 32 may have a shape and/or texture that enhances the ability to grasp the collection vessel cap 32 and turn the collection vessel cap 32 with respect to the collection vessel 30. Because of the nature of the invention and the potential desire to remove the collection vessel cap 32, the collection vessel cap 32 is typically intended to be tightened and loosened using manual force.

The collection vessel cap 32 includes a first port 50 and a second port 52 formed therein. A person of skill in the art will appreciate that at least one of the first port 50 and the second port 52 may alternatively be formed in the collection vessel 30.

The first port 50 includes a connector that facilitates attachment to the tubing 16. In certain embodiments, the first port 50 enables tubing 16 to be attached and detached. When the tubing 16 is attached, a substantially gas-impervious seal is formed. The first port 50 may include a standardized connector profile that enables a variety of objects to be attached thereto. An example of one suitable standardized connector is marketed under the identifier Leur Lock.

Similar to the first port 50, the second port 52 may be formed with a standardized connector profile. An example of one such connector profile that can be used for the second port 52 is a tapered push-on connector that facilitates a friction connection. In such embodiments, the push-on connector includes a plurality of ridges, which reduce the potential of the tubing or other object becoming detached from the second port 52.

The collection vessel cap 32 may be fabricated from a variety of materials using the concepts of the invention. In one embodiment, at least a portion of the collection vessel cap 32 is fabricated from a transparent material.

Another criterion for the material that is used in fabricating the collection vessel cap 32 is that the material be biologically compatible and facilitate sterilization of the collection vessel cap 32 prior to use. An example of one such material that may be used to fabricate the collection vessel cap 32 is polyethylene terephthalate.

A filter container 48 is provided with respect to the processing device 14. The filter container 48 is positioned so that before the bone fragments and tissue flow into the collection vessel 30, these components pass through the filter container 48. In certain embodiments, the filter container 48 is attached to an inner surface of the collection vessel cap 32. The filter container 48 may be removably attached to the collection vessel cap 32 such as using a threaded mechanism.

In other embodiments, the filter container 48 may be attached to an outer surface of the collection vessel cap 32. In such an embodiment, the first port 50 may be directly attached to the filter container 48. In still other embodiments, the filter container 48 may be separate from the processing device 14. In this configuration, the tubing 16 is attached to the filter container 48. Another section of tubing (not shown) attached the filter container outlet to the first port 50.

The filter container 48 may have a volume that is significantly smaller than the volume of the processing device 14. In certain embodiments, the filter container 48 has a volume of less than about 20 cubic centimeters. In other embodiments, the filter container 48 has a volume of about 15 cubic centimeters.

A surface of the filter container may have perforations formed therein. In certain embodiments, a lower surface 49 of the filter container 48 may be perforated having a plurality of openings formed therein. The size of the openings may be selected to retain substantially all of the bone fragments in the filter container 48 as the bone fragments and tissue are aspirated from the patient. On the other hand, the openings are sufficiently large so that the liquid in the aspirated is permitted to flow through the lower surface 49 and into the collection vessel 30. The perforations thereby affect physical separation of the aspirate.

In certain embodiments, the lower surface 49 is integrally formed with the other components of the filter container 48. In other embodiments, the lower surface 49 may be removably attached to the filter container 48 such as using a threaded mechanism. This threaded mechanism may be similar to the threaded mechanism that is used to attach the filter container 48 to the collection vessel cap 32.

A filter material at least partially fills the filter container 48. The filter material is selected with a pore size such that substantially all of the bone fragments are retained in the filter material. The filter material may also be selected to retain at least a portion of the beneficial cells in the tissue. In certain embodiments, the filter material retains substantially all of progenitor cells in the extracted tissue.

The filter material may thereby provide physical separation of the bone fragments from the remainder of the material in the aspirate. Such a separation mechanism is referred to as physical separation. The filter material may also have an affinity for the beneficial components in the aspirate such that as the beneficial components flow past the filter material, the beneficial components are attached to the filter material so that the beneficial components retained in the filter container 48 would be included in the bone graft fabricated therefrom.

As an alternative to providing a relatively homogeneous filter material in the filter container 48, it is possible for the filter material to include more than one region. For example, there may be a top filter material portion and a bottom filter material portion. The top filter material portion may have a predisposition for retaining the bone fragments therein. The bottom filter material portion may have a predisposition for retaining the beneficial portions of the tissue therein.

In addition to or as an alternate to the filter material described above, the filter container 48 may have a filter membrane that is fabricated with a pore size that retains a desired portion of the bone fragments and the tissue within the filter container 48. For example, forming the filter membrane with a pore size of between about 20 microns and about 100 microns would facilitate retaining the bone fragments and a substantial portion of the progenitor cells in the filter container 48.

In yet another configuration, the filter container 48 is selected to retain the bone fragments therein but substantially all of the remainder of the tissue flows into the collection vessel 30. The tissue in the collection vessel 30 may thereby include in addition to progenitor cells, red blood cells and other components that are not needed or potentially detrimental to forming the bone void filler. In such a situation, the red blood cells may be caused to separate from the remainder of the tissue such as mixing a material that causes the red blood cells to agglomerate and settle to the bottom of the collection vessel 30. More details on such a process are described later in this application.

Because of the challenges in aspirating the tissue that is collected in the collection vessel 30, it is desirable for substantially all of the tissue to be retained in the collection vessel 30 for further processing. To reduce the potential of loss of the aspirated tissue that is collected in the bone fragment and tissue harvesting and processing system 10, a hydrophilic membrane valve (not shown) may be attached to the first port 52 intermediate the processing device 14 and the vacuum source.

The hydrophilic membrane valve allows the vacuum to pull gas therethrough until the hydrophilic membrane becomes wet such as when the bone fragment and tissue harvesting and processing system 10 is knocked over or the bone fragment and tissue harvesting and processing system 10 is overfilled with liquid. The hydrophilic membrane valve thereby prevents the aspirated tissue from being drawn out of the bone fragment and tissue harvesting and processing system 10.

To minimize the potential of the processing device 14 being moved from a vertical orientation, the processing device 14 may be placed in a base (not shown) having a width that is greater than the width of the processing device 14. An example of one suitable technique that may be used to retain the processing device 14 in a vertical orientation is described herein.

An alternative or additional technique to minimize the potential of aspirated tissue being drawn into the vacuum line may include attaching the processing device 14 to an object proximate to the patient from which the tissue is being aspirated. An example of one suitable option is a clip that attaches the processing device 14 to an IV pole, a drape near the patient or the operating table.

Prior to use, the components of the bone fragment and tissue harvesting and processing system 10 may be sterilized. A person of skill in the art will appreciate that a variety of sterilization techniques may be used. An example of one suitable sterilization technique is exposure of the packaged components to gamma radiation.

As an initial step in harvesting the bone fragments and tissue, the collection vessel cap 32 is attached to the collection vessel 30 so that the bone fragment and tissue harvesting and processing system 10 looks substantially as illustrated in FIG. 1. The tissue harvesting device 12 is attached to the processing device 14 using the tubing 16. A vacuum source is attached to the second port 52.

A site is selected from which the bone fragments and tissue are to be harvested. It is possible to use the invention in conjunction with harvesting bone fragments and tissue from a variety of bones in a patient. Preferred sites for harvesting the bone fragments and tissue include the iliac crest and pedicle/vertebral bodies.

The needle portion 22 is inserted into the bone. As the tip 24 contacts hard material within the bone, the tip 24 causes bone fragments to be formed. The needle portion 22 may also be rotated to cause bone fragments to be formed. In certain embodiments, the needle portion 22 is inserted while the needle portion 22 is rotated and while a vacuum is applied to the tissue harvesting device 12. Alternatively, the needle portion 22 may be inserted a desired distance into the bone, rotated and then a vacuum applied in sequence.

During the process of extracting the bone fragments and tissue, the needle portion 22 may be partially withdrawn, pivoted and inserted in a different direction. Such a process increases the amount of bone fragments and osteomedullary tissue that is harvested from the patient. Using such a process it is desirable for the needle to flex but at the same time not break or remain in a deformed/deflected configuration.

During the aspiration process it is important for the relatively liquid morselized tissue to be aspirated along with the bone fragments. Such a process minimizes the potential of the bone fragments becoming stuck while passing through the harvesting device 12 and the tubing 16 before reaching the collection vessel.

The aspiration process thereby depends on the formation of relatively small bone fragments, which is primarily caused by contact between the needle tip 24 and the harder areas inside the bone. The movement of the needle tip 24 through the interior of the bone also morselizes the tissue inside the bone and such morselizing causes the tissues to become more liquid.

To enhance the volume of bone fragments and tissue that can be aspirated, the needle portion 22 may be pivoted as the distal end of the needle portion 22 moves through the interior of the bone. Such movement causes bone fragments to be formed. The movement also morselizes the tissue inside of the bone, which enhances the ability to withdraw the tissue. This process significantly increases the volume of beneficial bone fragments and tissue that can be harvested as compared to conventional processing techniques that merely insert the aspiration needle into the bone at different depths. The needle portion 22 can also be rotated to increase the formation of bone fragments and the morselizing of tissue.

A vacuum is applied to the system, which causes the bone fragments and tissue to be aspirated through the needle portion 22. The aspirated bone fragments and tissue flow through the tubing 16 and into the processing device 14. This process is continued until a desired volume of bone fragments and tissue have been aspirated from the patient.

Thereafter, the bone fragments and tissue pass through the filter material in the filter container 48, which retains the bone fragments and at least a portion of the beneficial portions of the tissue therein. Depending on the intended use of the bone void filler, it may be possible to directly use the material in the filter container 48. Alternatively, it is possible to mix additional components to fabricate the bone void filler.

If it is not possible to obtain a desired volume of the bone fragments and tissue from a particular location, it may be necessary to insert the needle portion 22 into a different location in the bone. It may also be necessary to insert the needle portion 22 into a different bone.

It may be desirable to control the intensity of the vacuum that is pulled through the harvesting device 12. An example of one mechanism to control the vacuum level is using a valve that is operably attached to the vacuum line that is attached to the second port 52.

Conventional techniques for aspirating bone marrow that utilize a relating small diameter needle having an outer diameter of not more than 5 millimeters that includes several apertures proximate a distal end thereof. Even when this bone marrow aspiration needle is rotated and/or withdrawn during the aspiration, the relatively solid nature of the tissue inside the bone limits the amount of bone marrow that can be aspirated from a particular location.

Another drawback of the bone marrow aspiration needle is that as this bone marrow aspiration needle is extended through tissue, it causes compaction of tissue that is displaced by the bone marrow aspiration needle. This compaction makes it more challenging to withdraw the bone marrow that is proximate the openings near the distal end of this bone marrow aspiration needle.

Conventional techniques for obtaining material for use in preparing autograft utilize a coring device having an outer diameter of between about 10 and 18 millimeters. This coring device is inserted into a bone a desired distance and then withdrawn to retrieve the bone matrix.

While there are some beneficial cells associated with the bone matrix that is harvested from the patient, the volume of beneficial cells that are harvested from the patient is considerably smaller than the volume of beneficial cells that are harvested using the harvesting device described herein.

Nerves are primarily located on the surface of the bone. The process of cutting through the surface of the bone disturbs the nerves and thereby leads to the patient experiencing pain. Because of the diameter of the coring device, the patient typically experiences significant pain in the autograft harvesting region and such pain limits the use of this procedure.

The harvesting device 12 described herein has an outer diameter of about 6 millimeters, which is significantly smaller than the coring device and this smaller size hole that extends through the bone surface represents a reduction of the hole of between about 60 and 90 percent when compared to the coring device.

The smaller hole associated with the harvesting device 12 described herein thereby results in significantly lower pain than the coring device described above and such significantly lower pain makes the bone fragment and tissue harvesting procedure described herein to be much more tolerable to patients.

Another benefit of the process described herein is that using a single hole formed in the outer surface of the bone, the bone fragment and tissue harvesting needle 22 can be pivoted and then inserted into the bone in a different angular orientation to facilitate retrieving bone fragments and tissue from different locations of the bone.

Another advantage of the harvesting device 12 described herein is that the cutting features on the tip cause tissue to be disturbed from a larger area and when this disturbed area is exposed to a negative pressure provided by the vacuum, such a process enables aspirating tissue from a much larger region than is possible using the conventional bone marrow aspiration needle.

Red blood cells have a particle size of about 7 micrometers. White blood cells have a particle size of between about 15 and 18 micrometers. The beneficial osteomedullary and progenitor cells in the bone marrow aspirate have a particle size of between about 35 and 50 micrometers.

As a result of this situation is that the osteomedullary cells have a size that is considerably larger than the other components in the bone marrow aspirate, this size difference can be used to facilitate retention of the osteomedullary cells in the filter container while the much smaller red blood cells and white blood cells pass through the filter container.

In addition to utilizing the affinity of the osteomedullary tissue to the bone fragments and the size of the osteomedullary tissue to facilitate separation, it is also possible to process the material that collections in the collection vessel 30 to separate the red blood cells therefrom and then use the red blood cell depleted tissue in forming the bone graft. The process and device described herein thereby facilitates recovering substantially all of the beneficial cells from the tissue that is aspirated from the patient.

The system described herein thereby results in the aspiration of a significant amount of bone matrix. This system also results in multiple mechanisms for recovering beneficial cells from within the bone. The first mechanism encompasses the beneficial cells that are associated with the bone fragments. The second mechanism relates to the selective retention of the beneficial cells as the aspirate is passed through the filter container. The third mechanism is from the material that collects in the collection vessel and from which the red blood cells are separated as described in more detail herein.

The combined result of using these three mechanisms enables substantially all of the beneficial cells in the aspirated tissue is recovered. Such recovery represents a significant enhancement when compared to the prior techniques, which in addition to utilizing an inefficient harvesting process, recovered a much smaller percentage of the beneficial cells from the harvested tissue.

FIGS. 3 and 5 compare the structure of the prior art bone marrow aspiration needle and the bone fragment and tissue harvesting needle of this invention. The shaft of the prior art bone marrow aspiration needle 222 is substantially straight as illustrated in FIG. 3. This traditional bone marrow aspiration needle 222 has an outer diameter of about 4.15 millimeters. Proximate the tip of the prior art bone marrow aspiration needle 222, five openings 226 are provided. The openings 226 each have a diameter that is approximately 2 millimeters.

Three of the openings 226a are in an aligned configuration on a front side of the bone marrow aspiration needle 222 and two of the openings 226b are in an aligned configuration on a back side of the bone marrow aspiration needle such that the openings 226b on the back side are between the openings 226a on the front side.

Because of the generally non-liquid nature of the tissue within the bone from which it is desired to aspirate the bone marrow, there is a limited ability for the bone marrow to flow to the openings 226 in response to a vacuum being pulled through the bone marrow aspiration needle 222 during the bone marrow aspiration process. In particular, if the bone marrow aspiration needle is not rotated, the area from which the bone marrow can be aspirated is approximately the same as the size of the openings 226.

To increase the amount of tissue that is subjected to the vacuum during the aspiration process, the aspiration needle 222 is rotated. The increased aspiration area associated with the rotation of the bone marrow aspiration needle 222 is illustrated by the shaded areas 228 in FIG. 4. These shaded areas have a length of about 13.0 millimeters, which is equivalent to the circumference of the bone marrow aspiration needle 222. The total aspiration area provided by the prior art bone marrow aspiration needle 222 is thereby about 130 square millimeters.

While the calculations above are based upon the bone marrow aspiration needle 222 being rotated 360 degrees so that each of the openings 226 trace a path around the entire outer surface of the bone marrow aspiration needle 222, such results are not likely to be seen during the actual use of the bone marrow aspiration needle 222.

The prior art bone marrow aspiration needle 222 would be used in conjunction with a handle such as illustrated in FIG. 1. This handle enables the person performing the bone marrow aspiration to manipulate the bone marrow aspiration needle 222. When grasping the handle, the person's wrist would turn no more than about 180 degrees (and typically about 120 degrees).

The only way for the person to rotate the bone marrow aspiration needle 360 degrees is for the person to release and regrip the handle. Because of the cumbersome nature of the release and regrip process, the person using the bone marrow aspiration needle is unlikely to perform this process.

As described in more detail in this application, the bone fragment and tissue harvesting needle 22 has an outer diameter of about 6.3 millimeters. The distal end of the bone fragment and tissue harvesting needle 22 includes a first tip region 36, a second tip region 37 and a third tip region 38, which are illustrated in FIG. 5.

The first tip region 36 includes sharpened surfaces, which facilitates cutting tissue and forming bone fragments. The first tip region 36 includes at least one of a channel and an opening to facilitate aspirating the bone fragments and morselized tissue and/or directing the bone fragments and morselized tissue to the second tip region 37.

The second tip region 38 has an outer diameter that is less than the outer diameter of the first tip region 36 to facilitate flow of the bone fragments and morselized tissue to the opening 72. A combined length of the first tip region 36 and the second tip region 37 is about 17 millimeters.

The third tip region 38 has an outer diameter that is greater than the outer diameter of the second tip region 37 and is approximately the same as the outer diameter of the first tip region 36. This configuration causes the third tip region 38 to form a seal with respect to the tissue that that is adjacent to the outer surface of the third tip region 38 so that when a vacuum is pulled through the bone fragment and tissue harvesting needle 22, there is no leakage along the third tip region 38.

Using this configuration provides an aspiration area 39 of about 337 square millimeters, as illustrated in FIG. 6. While the bone fragment and tissue harvesting needle 22 is rotated to cause the formation of bone fragments and morselization of tissue, such rotation is not needed to provide this aspiration area in contrast to the traditional bone marrow aspiration needle that is discussed above with respect to FIGS. 3 and 4. This aspiration area is more than 2.5 times greater than the aspiration area provided by the prior art bone marrow harvesting needle.

Figure 7:
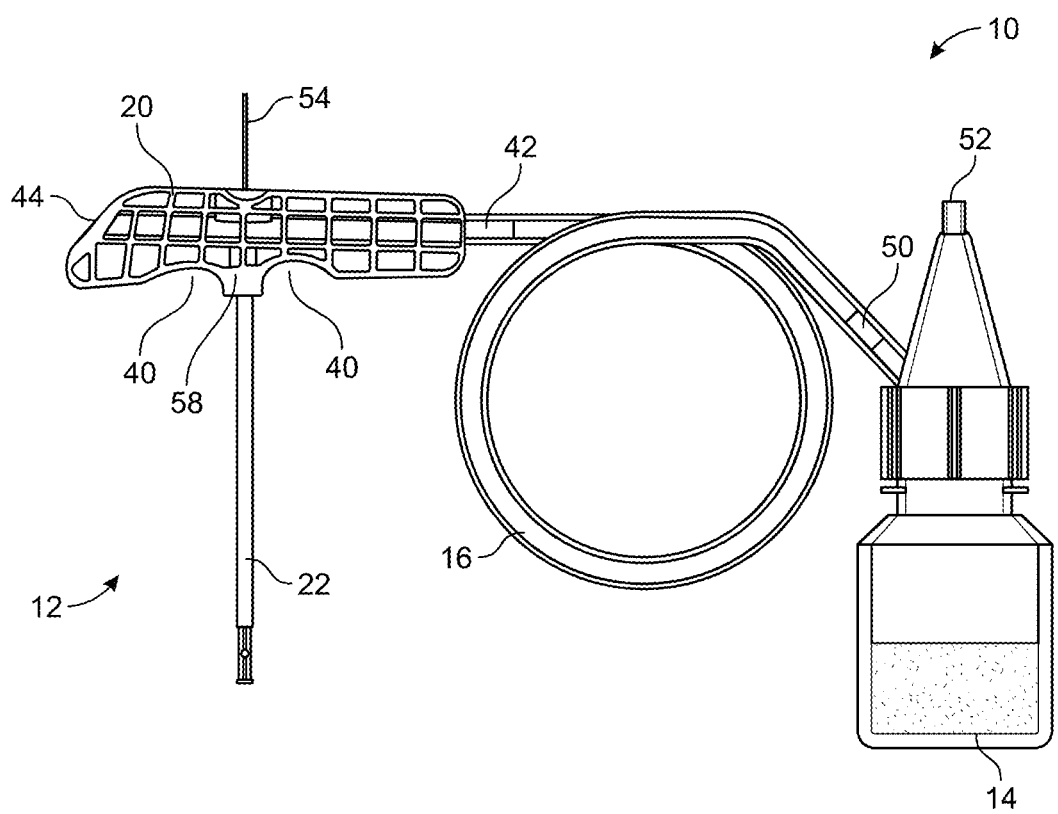
FIG. 7 is a side view of the bone fragment and tissue harvesting and processing system according to another embodiment of the invention.

Another embodiment of the invention is directed to a bone fragment and tissue harvesting device as illustrated at 12 in FIG. 7. The bone fragment and tissue harvesting device 12 may be used in conjunction with a bone fragment and tissue collection and processing device 14 and tubing 16.

As described in more detail below, the bone fragment and tissue harvesting device 12 is connected to the bone fragment and tissue collection and processing device 14 using the tubing 16. The outlet port 52 on the bone fragment and tissue collection and processing device 14 is connected to a vacuum source (not shown).

The bone fragment and tissue harvesting device 12 is used for accessing an interior region of a bone, forming bone fragments, morselizing tissue within the bone and then aspirating the bone fragments and tissue from the bone. The bone fragment and tissue harvesting device 12 generally includes a handle portion 20 to which a needle portion 22 is operably attached.

In certain embodiments, the handle portion 20 is oriented generally perpendicular to the needle portion 22, as illustrated in FIGS. 7-10. This configuration enables the bone fragment and tissue harvesting device 12 to be readily inserted into the bone and then manipulated to form bone fragments and morselize the tissue within the bone. This configuration may also facilitate tapping the handle portion 20 such as with a mallet to urge the needle portion 22 into the bone.

The handle portion 20 may be formed with an ergonomic shape that generally conforms to the shape of the user's hand when wrapped around the handle portion 20. In certain embodiments, the handle portion 20 may be formed with a generally cylindrical elongated shape having a length that is approximately equal to or slightly larger than a width of a user's hand. At least one of the side, top and bottom surfaces of the handle portion 20 may be curved to generally conform to the curvature of the user's hand when wrapped around the handle portion 20. Using such a configuration facilitates a person who is using the bone fragment and tissue harvesting device 12 to wrap his/her hand around the handle portion 20 and firmly grip the handle portion 20.

The lower surface of the handle portion 20 may include at least one depression 40 that is recessed as compared to adjacent areas of the lower surface. The depressions 40 may each be shaped to generally conform to a portion of the shape of one of the user's fingers when the user's hand is wrapped around the handle portion 20. In certain embodiments the handle portion 20 includes two depressions 40 that are on opposite sides of where the needle portion 22 engages the handle portion 20.

The handle portion 20 includes a vacuum connection port 42, which enables the bone fragment and tissue harvesting device 12 to be operably attached to the tubing 16. In certain embodiments, the vacuum connection port 42 is located proximate a proximal end of the handle portion 20.

The vacuum connection port 42 may facilitate readily attaching and detaching the tubing 16. A person of skill in the art will appreciate that a variety of configurations may be used to releasably attach the tubing 16 to the bone fragment and tissue harvesting device 12.

In certain embodiments, the vacuum connection port 42 has a generally cylindrical shape. An outer diameter of the vacuum connection port 42 may be slightly larger than an inner diameter of the tubing 16 so that a friction fit causes the tubing 16 to stay in engagement with the vacuum connection port 42.

Figure 9:
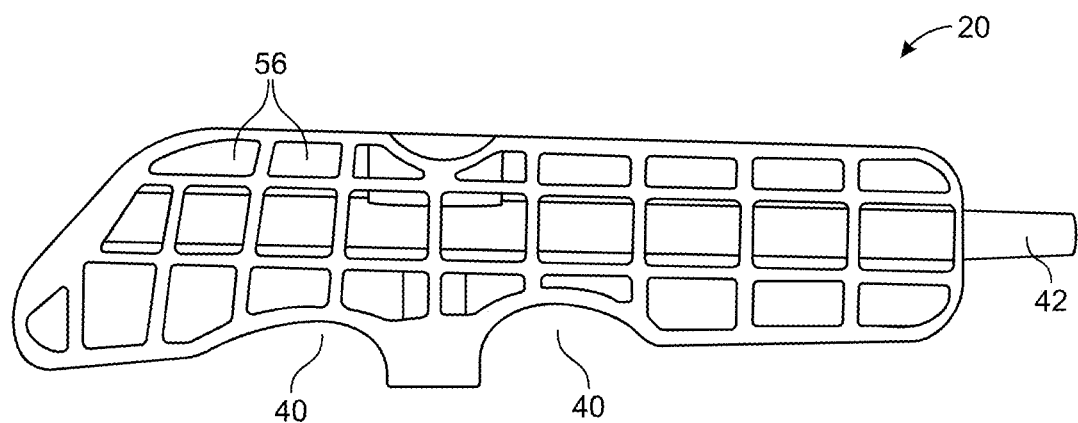
FIG. 9 is a side view of the handle portion of FIG. 8.
Figure 10:
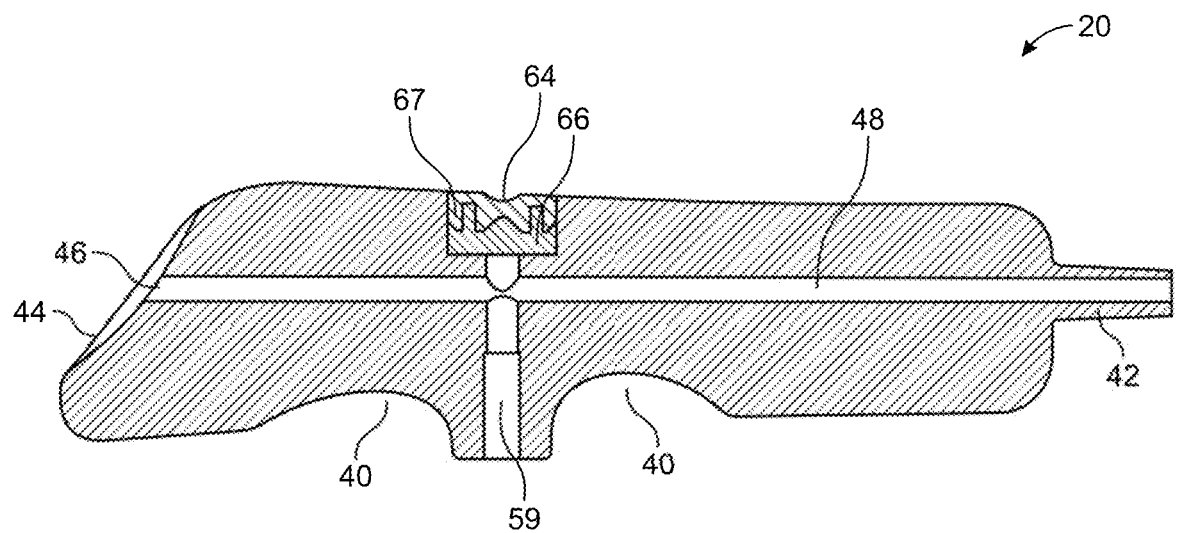
FIG. 10 is a sectional view of the handle portion of FIG. 8.

The vacuum connection port 42 may be tapered so that a diameter of the vacuum connection port 42 is greater proximate where the vacuum connection port 42 extends from the handle portion 20, as illustrated in FIG. 9. The vacuum connection port 42 may also include at least one ridge on an outer surface thereof to enhance the ability of the tubing 16 to remain engaged with the vacuum connection port 42.

The handle portion 20 also includes a suction control mechanism 44, which controls when a vacuum is drawn through the needle portion 22. When the suction control mechanism 44 is open, the vacuum pulls air through the suction control mechanism 44 as the resistance to flow is considerably lower than through the needle portion 22. When the suction control mechanism 44 is closed, the vacuum causes tissue to be drawn through the needle portion 22 for aspirating the bone fragments and tissue.

Figure 8:
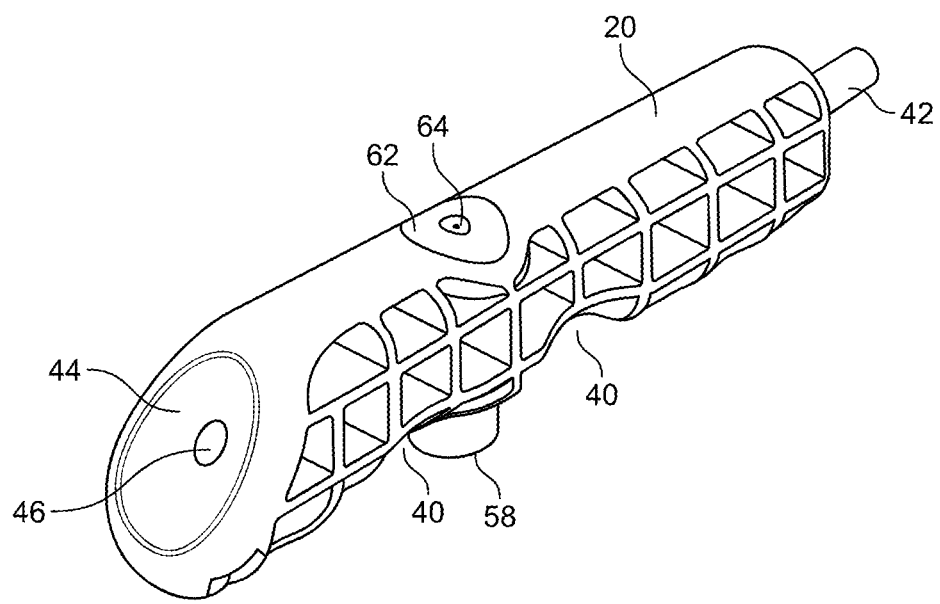
FIG. 8 is a perspective view of a handle portion of the bone fragment and tissue harvesting device of FIG. 7.

In certain embodiments, the suction control mechanism 44 is located proximate a distal end of the handle portion 20. The suction control mechanism 44 includes an aperture 46 that extends through a surface of the handle portion 20 and is in communication with a handle bore 48 that extends to the proximal end of the handle portion 20 and intersects the vacuum connection port 42, as illustrated in FIG. 8.

One technique for moving the suction control mechanism 44 to the closed configuration is for the person using the bone fragment and tissue harvesting device 12 to place his/her finger over the aperture 46 so that the aperture 46 is substantially covered. In this regard, the aperture 46 should have a shape and size that are sufficiently small such that the aperture 46 can be covered by the person's finger.

While the aperture 46 is illustrated as being circular, a person of skill in the art will appreciate that aperture 46 can have a variety of shapes using the concepts of the invention. In other embodiments, the suction control mechanism 44 may include a mechanical valve that is moved between open and closed positions such as by turning or sliding a component of the mechanical valve.

The suction control mechanism 44 may be recessed as compared to the adjacent surface of the handle portion 20 to enhance the ability of a person using the bone fragment and tissue harvesting device 12 to accurately place his/her finger over the aperture 46 without the person using the bone fragment and tissue harvesting device 12 having to visually confirm the accurate placement of the user's finger over the aperture 46. The shape of the recess may be generally circular or oval.

The handle portion 20 also includes a needle portion connection port 58 that enables the needle portion 22 to engage the handle portion 20. In certain embodiments, the needle portion connection port 58 is located on the lower surface of the handle portion 20 approximately intermediate the distal and proximal ends thereof.

The needle portion connection port 58 should enable a substantially air-tight seal to be formed between the handle portion 20 and the needle portion 22. The needle portion connection port 58 should also provide a substantially rigid connection to be formed between the handle portion 20 and the needle portion 22 such that the handle portion 20 can be used to cause the needle portion 22 to extend through the outer surface of the bone and to enable the bone fragment and tissue harvesting device 12 to be manipulated when forming bone fragments and morselizing tissue within the bone.

In certain embodiments, the needle portion 22 is removably attached to the handle portion 20. Using this configuration enables needle portions 22 having a variety of different lengths, diameters and/or cutting features to be used in conjunction with the bone fragment and tissue harvesting device 12. An example of one such technique for removably attaching the needle portion 22 to the handle portion 20 is a threaded connection on the adjoining surfaces of the needle portion 22 and the handle portion 20.

The needle portion connection port 58 has a bore 59 extending therethrough that intersects the handle bore 48. The bore 59 may extend through a surface of the handle portion 20 that is generally opposite the surface from which the needle portion 22 engages the handle portion 20. In certain embodiments, the bore 59 extends through the upper surface of the handle portion 20.

The bore 59 thereby enables a guide wire 54 to extend through both the handle portion 20 and the needle portion 22. The guide wire 54 may be useful in accurately forming the hole in the bone as well as orienting the bone fragment and tissue harvesting device 12 in a direction to facilitate optimal harvesting of the bone fragment and tissue using an imaging technique such as a fluoroscope.

While it is described that the opening used for the guide wire 54 is different than the aperture for the suction control mechanism 44, a person of skill in the art will appreciate that the location of the suction control mechanism 44 may be moved to the same location as the hole through which the guide wire 54 is extended.

A gasket 66 may be placed over the bore 59 to substantially restrict the flow of air through the bore 59. The gasket 66 may be fabricated from a material through which it is possible for the guide wire 54 to extend. The gasket 66 may be fabricated from a self-healing material such that after the guide wire 54 is removed from the gasket 66, the gasket 66 is substantially air-tight. An example of one such material that may be used to fabricate the gasket 66 is silicone. An opening (not shown) may be formed in the gasket 66. In certain embodiments, the opening has an X shape and is formed using a laser.

A cover 67 may be placed over the gasket 66 to retain the gasket 66 in a desired position with respect to the handle portion 20. The cover 67 has an aperture 64 formed near the center thereof to thereby direct the guide wire 54 to extend through the center of the gasket 66 where the opening is formed.

At least a portion of the gasket 66 and the gasket cover 67 may be recessed in the handle portion 20. Using such a configuration may enable the upper surface of the handle portion 20 to be substantially smooth as illustrated in FIGS. 7-10.

In certain embodiments, the outer surface of the handle portion 20 may have a plurality of recesses 56 formed therein. The recesses 56 reduce the amount of material that is needed to fabricate the handle portion 20 and such a reduction of material reduces the weight of the aspiration device.

Another potential advantage of the recesses 56 is that the recesses may enhance the ability of the person using the bone fragment and tissue harvesting device 12 to grasp the handle portion 20, as any tissue and fluid that is on the user's hand may move into the recesses 56.

The handle portion 20 may be fabricated from a variety of materials that are suitable for use in medical applications. An example of one such material that can be used to fabricate the handle portion 20 is a biocompatible polymer, which is suitable for being molded and then sterilized prior to use.

Figure 11:
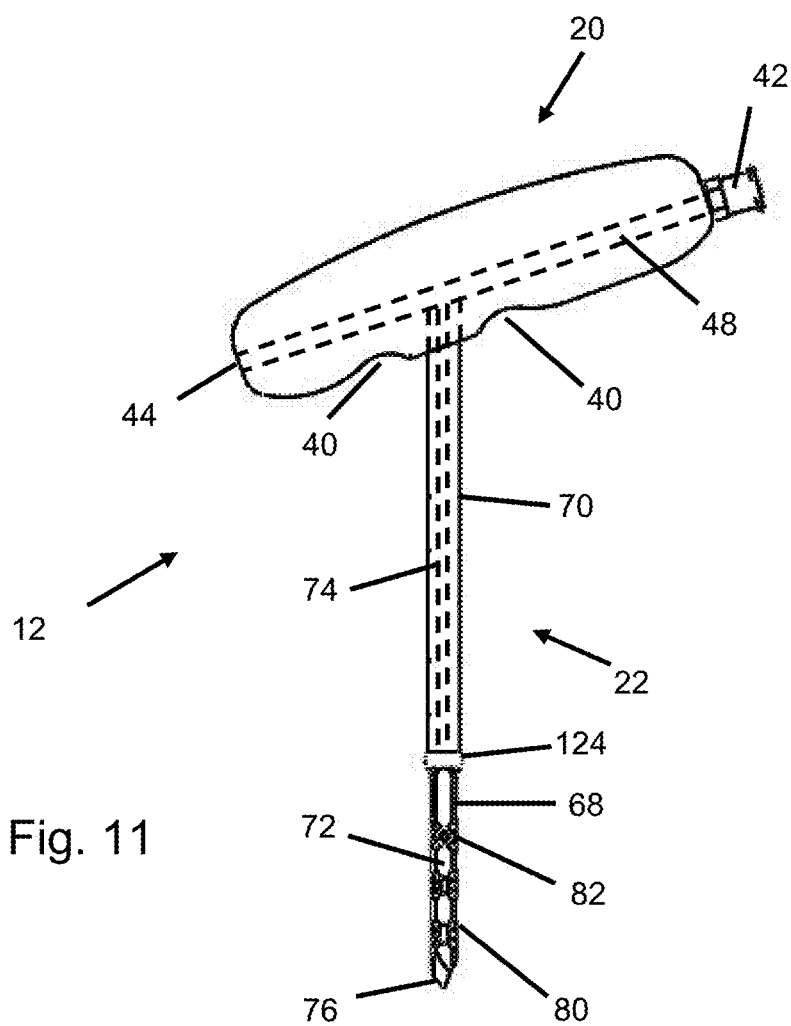
FIG. 11 is a side view of an alternative embodiment of the bone fragment and tissue harvesting device.

An alternative configuration of the bone fragment and tissue harvesting device 12 is illustrated in FIG. 11. This embodiment includes the needle portion 22 oriented at a non-perpendicular angle with respect to the handle portion 20. In certain embodiments, an angle between the needle portion 22 and the handle portion 20 is between about 60 degrees and about 90 degrees. In other embodiments, the angle between the needle portion 22 and the handle portion 20 is between about 65 degrees and about 75 degrees.

Similar to the embodiment illustrated in FIGS. 7-10, the handle portion 20 has a vacuum connection port 42 at a proximal end, a suction control mechanism 44 at a distal end and a needle portion connection port 58 in a lower surface intermediate the proximal and distal ends. However, FIG. 11 illustrates that the vacuum connection port 42 is a different style than the vacuum connection port 42 illustrated in FIGS. 7-10. This style of connector is typically referred to as a Luer lock.

The needle portion 22 may be fabricated from a variety of materials using the concepts of the invention. In one such embodiment, the needle portion 22 is fabricated from a relatively rigid material so that the needle portion 22 resists bending and/or deformation during use. An example of one such relatively rigid material that resists bending and/or deformation is stainless steel.

In other embodiments, at least part of the needle portion 22 may be fabricated from a material that allows the needle portion 22 to flex or bend. Using such a configuration enables the needle portion 22 to bend such as when the distal end of the needle portion 22 contacts a rigid portion of the bone.

The needle portion 22 should have sufficient rigidity so that the needle portion 22 moves along a particular path until the needle portion 22 contacts an obstacle so that it is possible to insert the needle portion 22 into the bone in different angular orientations to increase the volume of advantageous cells that are aspirated. The needle portion 22 should also be sufficiently rigid so that contact between the tip of the needle portion 22 and bone causes bone fragments to be formed. However, the needle portion 22 should not be too rigid such that the does not deflect when contacting an obstacle such as the opposite side of the bone.

The flexibility of the needle portion 22 may be defined in view of the ability of the needle portion 22 to deflect to generally conform to a curved surface. In certain embodiments, the needle portion 22 is deflectable using manual pressure to generally conform to a curved surface having a radius of less than about 20 centimeters. In other embodiments, the needle portion 22 is deflectable using manual pressure to generally conform to a curved surface having a radius of between about 10 centimeters and about 15 centimeters.

In this configuration, the needle portion 22 may be fabricated from a polymeric material such as by molding. Examples of materials that may be used to fabricate the needle portion 22 include PEEK and IXEF.

When the needle portion 22 is fabricated from a material that allows the needle portion 22 to bend or flex, selected parts of the needle portion 22 may be more rigid. For example, the part of the needle portion 22 that engages the handle portion 20 may be more rigid such as when a threaded connection is used to attach the needle portion 22 to the handle portion 20. Additionally, to facilitate forming bone fragments and morselizing tissue within the bone, the cutting features on the needle portion 22 may be more rigid.

One technique that may be used to make parts of the needle portion 22 more rigid is by making the wall thickness greater. Since it is desired that the outer dimensions of the needle portion 22 to be relatively constant in the part of the needle portion 22 that extend into the bone, the wall thickness may be increased by reducing the diameter of the aperture 74 that extends through the needle portion 22. The part of the needle portion 22 that does not extend into the bone may be strengthened by increasing the wall thickness by increasing the outer diameter of the needle portion 22.

Another technique that may be used to increase the rigidity of selected parts of the needle portion 22 is to add a reinforcing material and/or using a different material to fabricate selected parts of the needle portion 22.

In view of the flexing nature of the needle portion 22, it may be desirable to evaluate the location of the distal end of the needle portion 22 during the bone fragment and tissue harvesting process. For embodiments where the needle portion 22 is fabricated from a non-metallic material, it may be desirable for at least part of the needle portion 22 to be fabricated from a radiolucent material. Alternatively or additionally, a radiopaque marker may be incorporated into the needle portion 22. Using these techniques enables the position of the needle portion 22 in the bone to be evaluated using an imaging technique such as with a fluoroscope.

The needle portion 22 should have sufficient rigidity so that the needle portion 22 provides feedback to the person using the bone fragment and tissue harvesting device 12 when the needle portion 22 contacts something prior to deflecting in response to such contact.

The needle portion 22 has an elongated configuration with a handle attachment mechanism proximate a proximal end thereof and a tip section 68 proximate a distal end thereof. As described earlier, the needle portion 22 may be removably attached to the handle portion 20 using a threaded mechanism. The handle attachment mechanism thereby facilitates a robust connection between the needle portion 22 and the handle portion 20.

Intermediate the handle attachment mechanism and a tip section 68 is a main section 70. The main section 70 is formed with a length that is sufficiently long so that the handle portion 20 can be manipulated during the bone fragment and tissue aspiration process without the handle portion 20 contacting the patient's body as such contact could interfere with the bone fragment and tissue aspiration process and potentially lead to damage of the bone fragment and tissue harvesting device 12. In certain embodiments, the main section 70 has a length of between about 10 centimeters and about 25 centimeters.

The main section 70 may be fabricated with sufficient strength to facilitate urging the tip section 68 into the outer surface of the bone as well as to enable pivoting of the needle portion 22 during the process of aspirating the tissue while avoiding bending or breakage of the needle portion 22. An outer surface of at least a portion of the main section 70 may be generally cylindrical and be substantially smooth.

The tip section 68 may have a relatively small length as compared to the overall length of the needle portion 22. In certain embodiments, the length of the tip section 68 is less than about 50 millimeters. In other embodiments, the length of the tip section 68 is about 10 millimeters.

The tip section 68 has at least one aperture 72 formed therein through which the bone fragments and tissue can be drawn into a central bore 74 that extends to the proximal end of the needle portion 22. In certain embodiments, there are a plurality of apertures 72 oriented in a spaced-apart configuration on the tip section 68.

The apertures 72 may be formed with different sizes. In certain embodiments, the size of the apertures 72 increases when moving towards the distal end of the tip section 68. Using such a configuration causes a substantially equal amount of suction to be provided at each of the apertures, which enhances the efficiency of the tissue aspiration process.

The apertures 72 may have a variety of shapes using the concepts of the invention. In certain embodiments, the apertures 72 are round, oval, square or rectangular. Because of the limited space on the sides of the tip section, the area of the apertures 72 may be changed by varying a length of the apertures 72.

Figure 12:
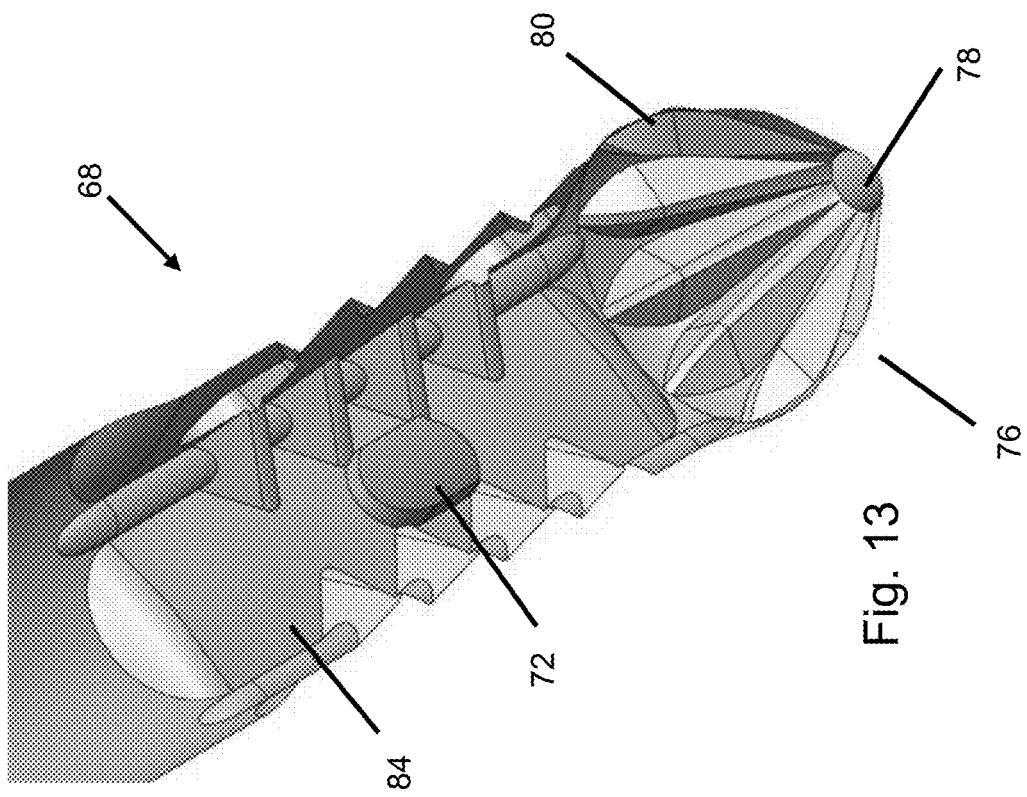
FIG. 12 is a first perspective view of a distal end of a needle portion of the bone fragment and tissue harvesting device.
Figure 13:
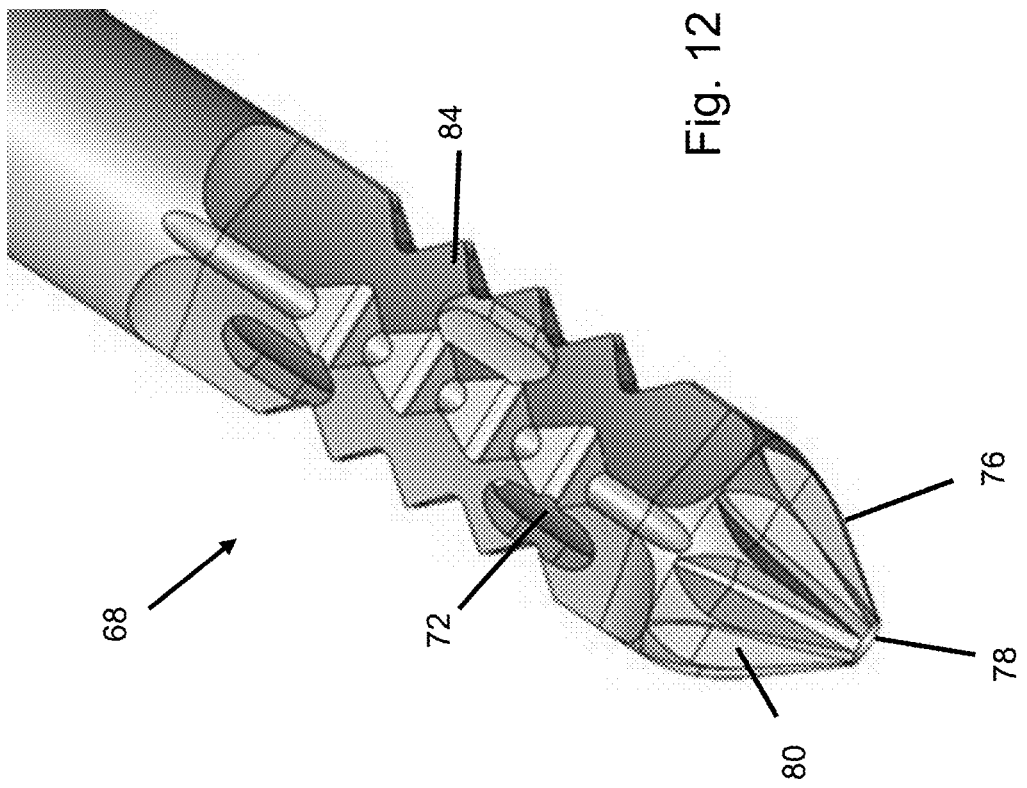
FIG. 13 is a second perspective view of the distal end of the needle portion of FIG. 12.

A distal end 76 of the tip section 68 is pointed, which enables the distal end 76 to pierce the bone from which the tissue is to be harvested. In certain embodiments, the distal end 76 includes a plurality of sharpened surfaces, as illustrated in FIGS. 12 and 13. This configuration enhances the ability of the distal end 76 to penetrate cortical bone from which the bone fragments and tissue are to be harvested. In certain embodiments, the distal end 76 includes about 10 cutting flutes formed therein. Each of the flutes comes to a cutting edge and such cutting edges provide the distal end 76 with a significant portion of its cutting ability. An aperture 78 may extend through the distal end 76. The guide wire 54 is capable of extending through the aperture 78.

The tip section 68 also includes at least one cutting surface 80 on a side surface thereof. The at least one cutting surface 80 facilitates morselizing the tissue within the bone such that a greater percentage of the advantageous cells inside of the bone can be aspirated.

The at least one cutting surface 80 may comprise a plurality of cutting edges that are generally oriented to extend parallel to the central axis of the needle portion 22. In certain embodiments, there are four cutting edges, as illustrated in FIGS. 12 and 13.

The at least one cutting surface 80 may have a height that is no greater than the height of the main section 70. Using this configuration minimizes cutting of tissue as the needle portion 22 is inserted into or removed from the patient.

At least part of the tip section 68 may have a generally planar surface 84. In certain embodiments, there are four planar surfaces 84. The planar surfaces 84 may intersect proximate the cutting edges. The planar surfaces 84 may provide a pathway for the bone fragments and morselized tissue to flow to the apertures 72 during the aspiration process.

The at least one cutting surface 82 may also comprise at least one abrasive region (not shown) on the outer surface of the tip section 68. The abrasive regions may be positioned between the cutting edges. In certain embodiments, the abrasive regions are concentrated in proximity to the apertures 72.

Figure 14:
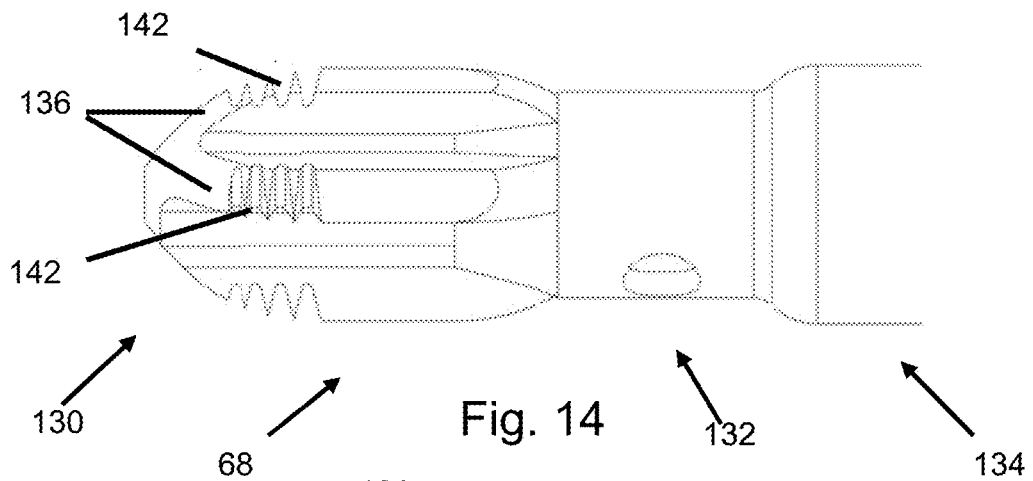
FIG. 14 is a top view of an alternative configuration of the distal end of the needle portion.
Figure 15:
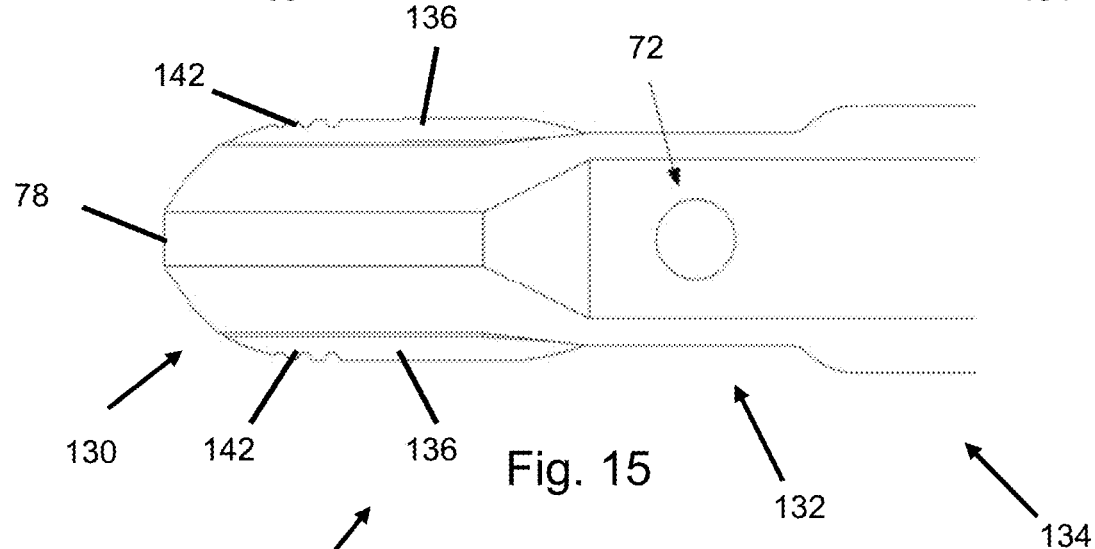
FIG. 15 is a sectional view of the distal end of the needle portion of FIG. 14.
Figure 16:
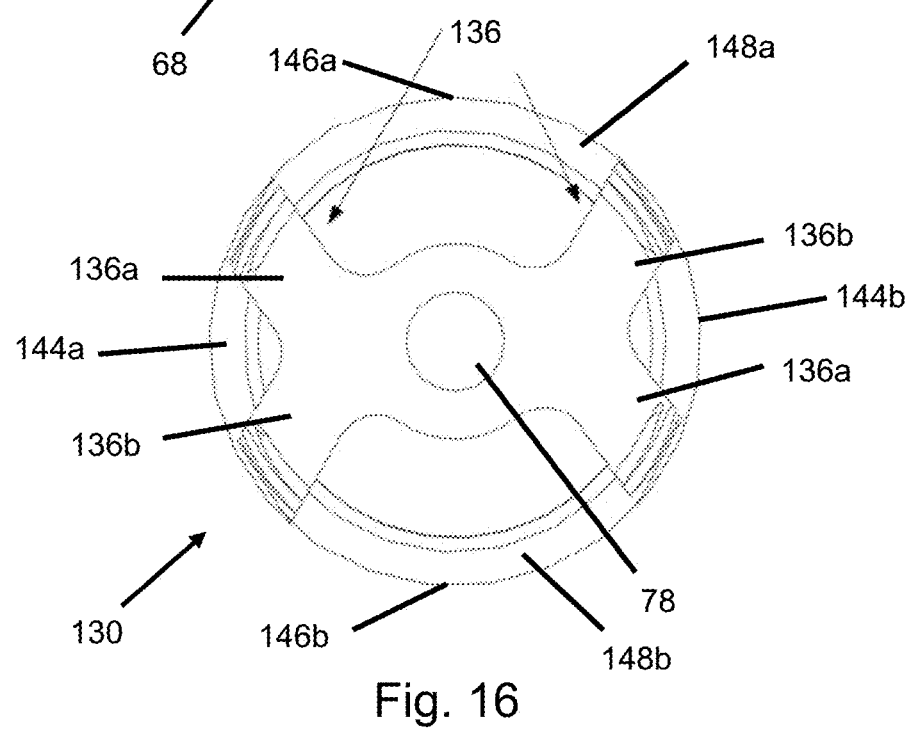
FIG. 16 is an end view of the distal end of the needle portion of FIG. 14.
Figure 17:
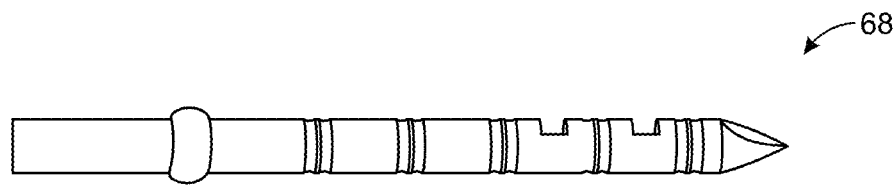
FIG. 17 is a side view of an alternative configuration of the distal end of the needle portion.

In another embodiment, which is illustrated in FIGS. 14-16, the tip section 68 includes a first tip region 130, a second tip region 132 and a third tip region 134. The first tip region 130 may be referred to as the tissue cutting and/or disruption zone. The second tip region 132 may be referred to as the aspiration zone. The third tip region 134 may be referred to as the vacuum sealing zone.

The first tip region 130 is located proximate the distal end of the tip section 68 and is the part of the tip section 68 that is primarily responsible for cutting tissue within the bone. The first tip region 130 includes a plurality of cutting elements 136 formed therein. The cutting elements 136 each have at least one cutting edge 138. In certain embodiments, the cutting elements 136 may be oriented to facilitate preferential cutting when the needle portion 22 is rotated in a particular direction. A portion of the cutting elements 136 may be oriented to facilitate preferential cutting in a clockwise direction and a portion of the cutting elements 136 may be oriented to facilitate preferential cutting in a counterclockwise direction.

As used herein, preferential cutting refers to the surfaces of the cutting element 136 that form the cutting edge 138 forming an acute angle. In certain embodiments, the angle between the two surfaces is between about 45 degrees and about 90 degrees. In other embodiments, the angle between the two surfaces is between about 60 degrees and about 80 degrees.

In certain embodiments, there are four cutting elements 136. Two of the cutting elements 136a are located proximate a first side 144a of the first tip region 130 and two of the cutting elements 136b are located proximate a second side 144b of the first tip region 130. Providing the cutting elements 136a, 136b in this configuration not only facilitates similar cutting action while rotating the needle portion 22 in opposite directions but also provides relatively open regions 148a, 148b on top and bottom surfaces 146a, 146b of the tip section 68 so that the aspiration process can cause the bone fragments and morselized tissue to be drawn away from the cutting elements 136 for aspiration through the apertures 72.

At least one of the cutting elements 136 may have at least one cutting tooth 142 formed therein. In certain embodiments, each of the cutting elements 136 has a plurality of cutting teeth 142 formed therein. The cutting teeth 142 may be located proximate the distal end of the tip section 68 but are located in a spaced-apart orientation from the distal end of the tip section 68. This configuration minimizes the cutting teeth 142 cutting tissue as the needle portion 22 is being inserted but rather facilitates preferential cutting with the cutting teeth 142 as the needle portion 22 is rotated.

Each of the cutting teeth 142 may have a pointed distal end. The cutting teeth 142 may be tapered between opposite ends thereof to facilitate preferential cutting by the cutting teeth 142 in a similar direction as to the preferential cutting with the cutting element 136 to which the cutting teeth 142 are formed.

One of the cutting elements 136a may be oriented to preferentially cut in the clockwise direction and one of the cutting elements 136a may be oriented to preferentially cut in the counterclockwise direction. Similarly, one of the cutting elements 136b may be oriented to preferentially cut in the clockwise direction and one of the cutting elements 136b may be oriented to preferentially cut in the counterclockwise direction.

Similar to the embodiment illustrated in FIGS. 12 and 13, the aperture 78 may extend through the distal end of the tip section 68. A primary function of the aperture 78 is to allow the guide wire 54 to extend therethrough when positioning the bone fragment and tissue harvesting device 12 with respect to the bone. A person of skill in the art will also appreciate that the aperture 78 may permit the bone fragments and tissue to pass therethrough during the aspiration process.

The first tip region 130 may have a relatively short length compared to the overall length of the needle portion 22. In certain embodiments, the first tip region 130 has a length of between about 5 millimeters and about 20 millimeters. In other embodiments, the first tip region 130 has a length of about 10 millimeters.

The first tip region 130 may have a generally circular outer profile that tapers when moving towards the distal end of the tip section 68. The first tip region 130 may also taper when moving towards the second tip region 132.

While it is desired for the first tip region 130 to have a relatively small diameter to minimize the hole that needs to be made in the outer surface of the bone, forming the first tip region 130 is a small diameter limits not only the rate at which the bone fragments and tissue can be aspirated through the needle portion 22 but also raises the potential that the bone fragments and tissue may plug the needle portion 22. In certain embodiments, the first tip region 130 has a diameter of between about 3 millimeters and about 10 millimeters. In other embodiments, the first tip region 130 has a diameter of about 5 millimeters.

The second tip region 132 has at least one aperture 72 formed in an outer surface thereof. In certain embodiments, the at least one aperture 72 includes two apertures. One of the apertures 72 may be oriented proximate the upper surface of the tip section 68 and one of the apertures 72 may be oriented proximate the lower surface of the tip section 68. This configuration causes the apertures 72 to be positioned in the opening between the cutting elements 136 and thereby enhances the ability to aspirate the bone fragments and tissue that have been formed by the cutting elements 136.

In certain embodiments, the apertures 72 each have a generally circular shape. If it is desired to provide an enhanced ability to aspirate the bone fragments and tissue, the apertures 72 may be formed with an elongated shape similar to the aperture 72 illustrated in FIGS. 12 and 13.

The second tip region 132 may have an outer surface that is smaller than the outer surface of the first tip region 130. This configuration facilitates moving the bone fragments and morselized tissue from the cutting elements 136 to the apertures 72. While it is illustrated that the second tip region 132 has a generally cylindrical shape, a person of skill in the art will appreciate that the second tip region 132 may have a variety of shapes that are capable of providing the preceding characteristics. In certain embodiments, the second tip region 132 has an outer diameter of the second tip region 132 is about 4 millimeters.

The second tip region 132 may have a relatively short length. This length should be sufficiently long to facilitate moving the bone fragments and morselized tissue from the cutting elements 136 to the apertures 72. The length of the second tip region 132 may have a length that is less than the length of the first tip region 132. In certain embodiments, the second tip region 132 has a length that is between about 3 millimeters and about 10 millimeters. In other embodiments, the second tip region 132 has a length that is between about 4 millimeters and about 5 millimeters.

Similar to the second tip region 132, the third tip region 134 may have a generally cylindrical shape to minimize cutting or disruption of tissue as the needle portion 22 is inserted into and removed from the bone as well as when the needle portion 22 is rotated. An outer diameter of the third tip region 134 is greater than the outer diameter of the second tip region 132.

Forming the third tip region 134 with the outer diameter that is greater than the outer diameter of the second tip region 132 causes the third tip region 134 to contact tissue adjacent thereto and form a seal between the third tip region 134 and the adjacent tissue to minimize the potential of the vacuum to be pulled along the outer surface of the third tip region 134 as opposed to causing the bone fragments and morselized tissue to be aspirated.

In certain embodiments, the outer diameter of the third tip region 134 is approximately the same as the outer diameter of the first tip region 130. The third tip region 134 may have a diameter of between about 3 millimeters and about 10 millimeters. In other embodiments, the third tip region 134 has a diameter of about 5 millimeters.

Alternative configurations for the tip section are illustrated in FIGS. 17-20. The tip section embodiment illustrated in FIG. 16 includes a generally cylindrical outer surface with a series of grooves formed therein. The grooves are placed in a spaced-apart configuration and are generally transverse to an axis of the needle portion 22. The distal end of this embodiment has a plurality of flat sides that come to a point.

Figure 18:
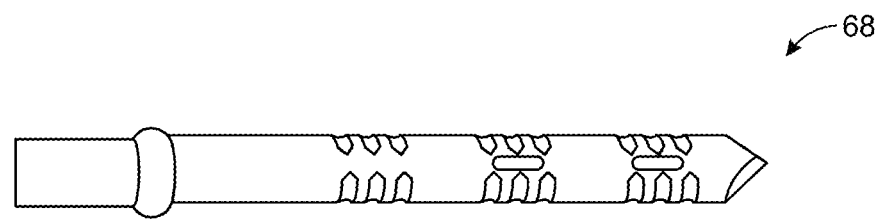
FIG. 18 is a side view of an alternative configuration of the distal end of the needle portion.
Figure 19:
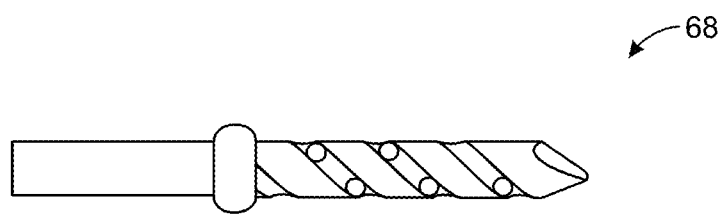
FIG. 19 is a side view of an alternative configuration of the distal end of the needle portion.
Figure 20:
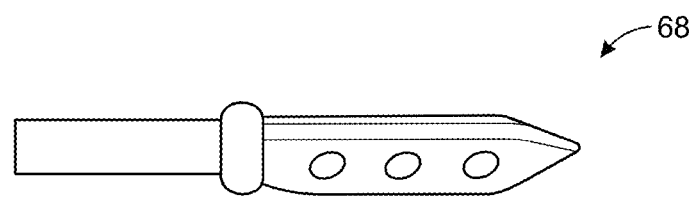
FIG. 20 is a side view of an alternative configuration of the distal end of the needle portion.

The tip section embodiment illustrated in FIG. 18 has an alternative groove configuration from the tip section embodiment illustrated in FIG. 16. The tip section embodiment illustrated in FIG. 19 includes a spiral groove formed therein. The tip section embodiment illustrated in FIG. 20 has two generally flat side surfaces in which apertures are formed.

Figure 21:
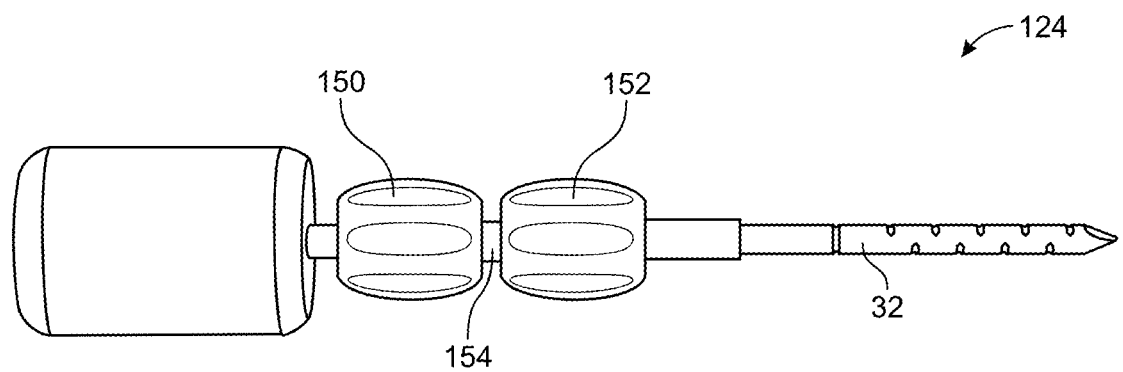
FIG. 21 is a side view of a stop mechanism for the bone fragment and tissue harvesting device where the stop mechanism is in an assembled configuration.
Figure 22:
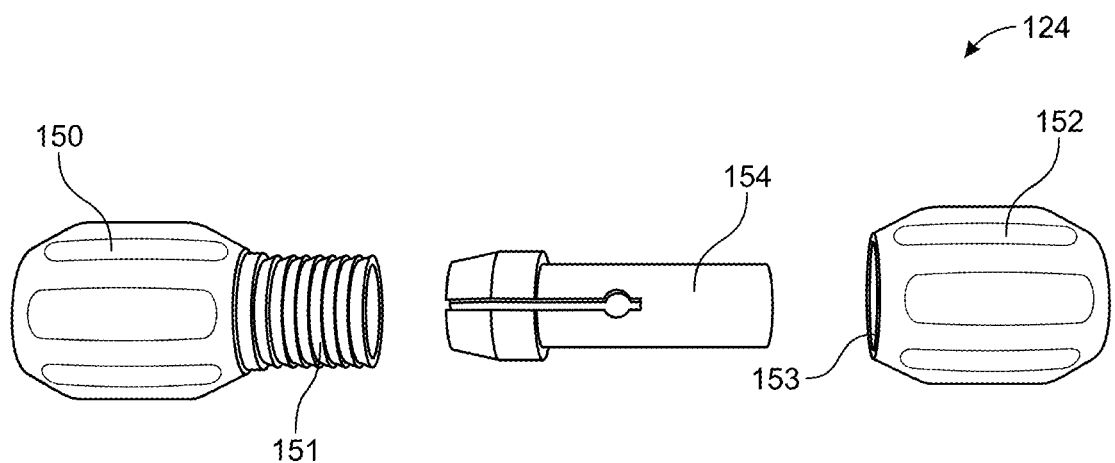
FIG. 22 is a side view of the stop mechanism of FIG. 21 in an unassembled configuration.

A stop member 124 may be configured for removable attachment to the needle portion 22 and having a configuration as illustrated in FIGS. 21 and 22. In certain embodiments, the stop member 124 includes a first grip 150, a second grip 152 and a collar 154.

The first grip 150 and the second grip 152 both have an outer surface that is suitable for grasping by a person using the stop member 124. An outer diameter of the first grip 150 and the second grip 152 is larger than the diameter of the needle portion 22 to enhance the ability of the user to grasp the first grip 150 and the second grip 152. This configuration also enhances the torque that can be applied when tightening the stop member 124 on the needle portion 22 and reduces the potential of the stop member 124 inadvertently moving with respect to the needle portion 22.

The first grip 150 includes a male threaded surface 151 that is engagable with a female threaded surface 153 on the second grip 152. Rotation of the first grip 150 with respect to the second grip 152 thereby causes the first grip 150 to move towards the second grip 152.

The collar 154 may have a generally cylindrical configuration with an inner diameter that is slightly larger than an outer diameter of the needle portion 22. At least a portion of the collar 154 is compressible in response to a force placed upon the collar 154 such as when the first grip 150 and the second grip 152 are moved toward each other. The compressability of the collar 154 may be provided by a slot or keyway that is formed in the collar 154.

The difference between the outer diameter of the stop member 124 and the outer diameter of the tip section 122 should be sufficiently large to limit a distance that the tip section 122 can be inserted into the bone (ilium) but should not be considerably larger than the outer diameter of the tip section 122 to minimize trauma to the tissue proximate the bone as the tip section 122 is extended into the bone.

In an alternative embodiment, the stop member 124 may be fixedly attached to the needle portion 22 such as illustrated in FIG. 11. In yet another embodiment, a friction inducing object (not shown) is placed between the stop member and the needle portion 22. An example of one such friction inducing member is an O-ring. This configuration enables the user to push the stop member to a desired depth without having to tighten any of the components.

In another embodiment, the bone fragment and tissue collection and processing device 14 includes an inlet port 50 that is connected to the bone fragment and tissue harvesting device 12 using the tubing 16. The bone fragment and tissue collection and processing device 14 also includes an outlet port 52 that is connected to a vacuum source (not shown) using tubing (not shown).

It may be desirable to separate non-liquid components in the bone fragment and tissue from liquid components in the bone fragment and tissue that are aspirated with the bone fragment and tissue harvesting device 12 because the non-liquid components may have advantageous characteristics when used in conjunction with bone glue prepared from the tissue. Examples of such non-liquid components include bone chips that are generated by the drilling process to access the interior of the bone. The non-liquid components may also include other tissue from within the bone that is not completely morselized.

To collect the non-liquid components, filter media may be placed inside of the bone fragment and tissue collection and processing device 14 while the tissue is harvested. In certain embodiments, the filter media has sufficiently large pores such that substantially all of liquid in the aspirated tissue flows therethrough. However, the filter media has sufficiently small pores such that substantially all of the non-liquid components in the tissue is retained on the filter media.

In one such embodiment, the filter media is placed proximate the opening in the collection vessel. The filter media may be retained in position with respect to the collection vessel using the collection vessel cap.

During the process of aspirating the bone fragments and tissue, the filter media is placed in the bone fragment and tissue collection device. Thereafter, once the aspiration process is complete, the filter media is removed from the bone fragment and tissue collection device.

The non-liquid components that were retained on the filter media may be mixed into the bone fragment and tissue after the red blood cells are separated therefrom. Alternatively, the non-liquid components may be mixed with the bone graft material prior to the red blood cell depleted tissue being mixed with the bone graft material.

In one configuration, the guide wire 54 is positioned for location and direction with respect to a bone from which the bone fragments and tissue are desired to be aspirated with the assistance of a fluoroscope. A drill bit is extended over the guide wire 54 and then used to drill a hole in the bone. The drill bit is withdrawn from over the guide wire 54 and the guide wire 54 is extended into the aperture 78 until the proximal end of the guide wire 54 extends through the handle portion 20.

The distal end of the needle portion 22 is extended a short distance into the bone. The handle portion 20 is rotated in clockwise and counterclockwise directions so that the tip section 68 causes tissue proximate thereto to be morselized. This process also causes bone fragments to be formed.

Thereafter, the user places his/her thumb over the suction control mechanism 44 to cause the bone fragments and tissue proximate the tip section to be aspirated. Because the beneficial cells in the tissue decrease significantly as the tissue is aspirated, care is used to not aspirate too much of the tissue from a particular location.

The user's thumb is then removed from the suction control mechanism 44 and then needle portion 22 is extended further into the bone. This further extension is between about 5 and 20 millimeters. The morselizing and aspiration process is repeated to cause an additional volume of bone fragments and tissue to be collected. This process is repeated until the needle portion 22 is inserted a maximum distance into the bone or until the distal end of the needle portion 22 comes into contact with a hard bone surface.

At this time, the needle portion 22 is substantially withdrawn from the bone and then oriented in a different angular position. The insertion, morselizing and aspiration process is repeated until a desired amount of the bone fragments and tissue have been collected. This process enables a greater volume of tissue to be recovered as compared to conventional bone marrow harvesting processes. This process also enables a larger volume of tissue having advantageous cells to be collected.

In another embodiment in conjunction with aspirating bone fragments and morselized tissue from a person's ilium 170, an incision is formed proximate the iliac crest. The distal end of the bone fragment and tissue harvesting device 12 is extended through tissue until adjacent the ilium 170. A force is used to urge the distal end to pierce the ilium 170. In certain embodiments, the force is provided by manual pressure.

Figure 23:
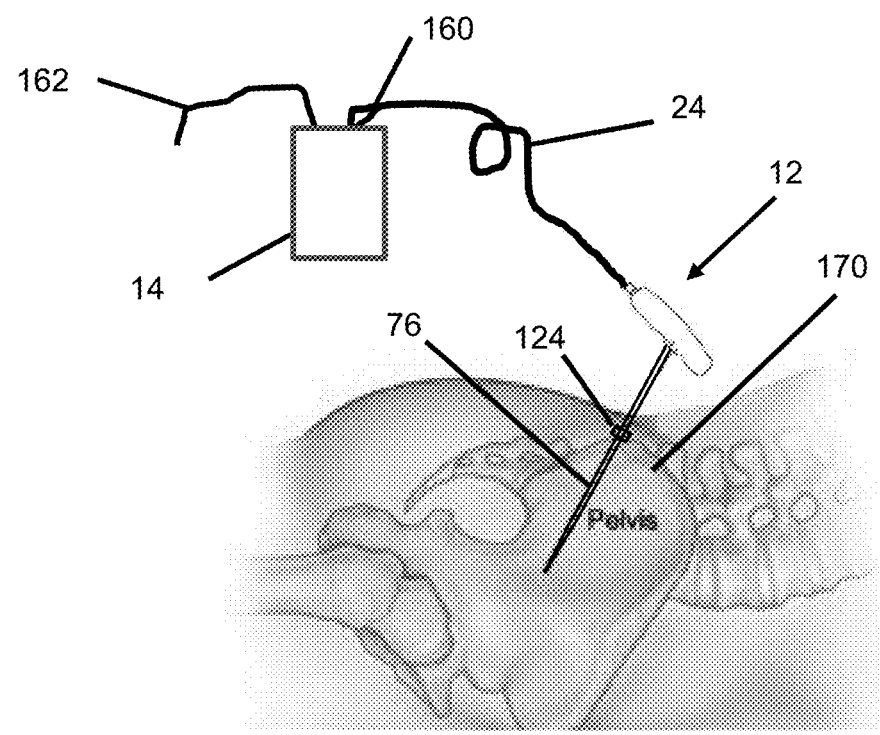
FIG. 23 is a schematic view of bone fragment and tissue harvesting system according to an embodiment of the invention where the needle portion is inserted into a patient's ilium.

The tip section 76 is extended into the ilium 170. In certain embodiments, the insertion is continued until the stop member 124 contacts the surface of the ilium 170, as illustrated in FIG. 23. Since the tip section 76 is extended using manual force, the person using the tissue aspiration device 12 should readily feel the stop member 124 contacting the surface of the ilium 170. The stop member 124 thereby overly extending the tip section 76 into the ilium 170.

Figure 24:
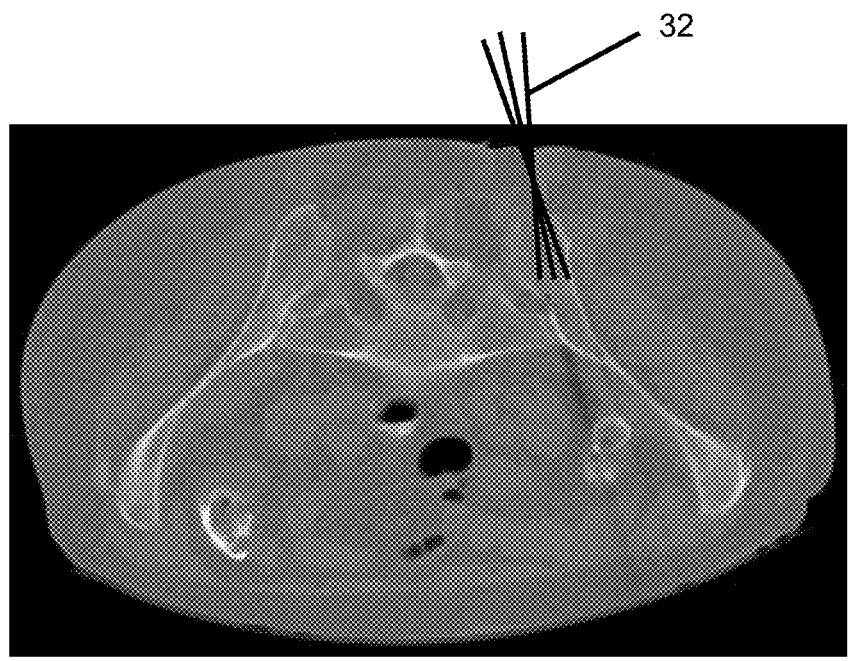
FIG. 24 is a radiological view showing the bone fragment and tissue harvesting device being pivoted while inserted into the patient's ilium.

The handle portion 20 is used to cause the needle portion 22 to pivot with respect to the ilium as illustrated in FIG. 24. The stop member 124 thereby acts as a fulcrum. As the needle portion 22 is pivoted, the tip section 76 moves through the tissue in the bone to thereby cause formation of bone fragments and morselizing of the tissue. In particular, this movement of the aspiration needle within the bone causes communition of trabecular bone.

Care should be exercised when pivoting the needle portion 22 such that the force is discontinued when resistance is felt as such resistance can be indicative of the tip section 76 contacting an inner surface of the ilium 170 and further pivoting of the needle portion 22 could lead to excessive bending of the needle portion 22 or damage to the ilium 170 and/or damage of the bone fragment and tissue harvesting device 12.

Care should also be exercised when pivoting the needle portion 22 to minimize the force that is placed on the edge of the aperture in the ilium 170 through which the tip section 76 extends as such force could cause the size of the aperture to increase, which would impact the ability of the stop member 124 to limit insertion of the needle portion 22 into the ilium 170.

The pivoting of the needle portion 22 is continued until sufficient bone fragment and tissue morselizing within the bone are achieved. At such time, the vacuum control mechanism 44 is closed to cause the bone fragments and morselized tissue to be aspirated from within the ilium 170. While the vacuum control mechanism 44 is closed, the needle portion 22 can continue to be pivoted to increase the amount of the bone fragments and tissue that are aspirated from the ilium 170.

In certain bones that have a sufficient depth, it is possible to partially insert the needle portion 22 into the bone and then rotate to form bone fragments and morselize the tissue. The needle portion 22 is further inserted into the bone and then rotated. In an alternative embodiment, it is possible to partially withdraw the tip section 76 from the ilium 170 and then repeat the pivoting and tissue aspiration. Once a desired amount of the bone fragments and tissue have been aspirated, the needle portion 22 is withdrawn from inside of the patient.

This process can be repeated on different regions of the ilium to aspirate additional bone fragments and tissue. The process can also be repeated on the opposite side of the ilium. A person of skill in the art will appreciate that the concepts described herein can also be used to aspirate bone fragment and tissue from other bones.

In the preceding detailed description, reference is made to the accompanying drawings, which form a part hereof, and in which is shown by way of illustration specific embodiments in which the invention may be practiced. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the present invention. The preceding detailed description, therefore, is not to be taken in a limiting sense, and the scope of the present invention is defined by the appended claims.

It is contemplated that features disclosed in this application, as well as those described in the above applications incorporated by reference, can be mixed and matched to suit particular circumstances. Various other modifications and changes will be apparent to those of ordinary skill.

The invention claimed is:

1. A bone fragment and osteomedullary tissue harvesting system comprising:
   a harvesting device comprising:
      a needle portion that comprises a needle bore and a tip, wherein the needle bore extends through at least part of the needle portion, wherein the needle portion has a proximal end and a distal end, wherein the tip is attached to and extends from the distal end of the needle portion, wherein the tip comprises:
         a first tip region having at least one cutting surface and a recessed region proximate the at least one cutting surface, wherein the recessed region extends to a proximal end of the first tip region and wherein the first tip region has an outer diameter;
         a second tip region having at least one aperture formed therein that intersects the bore, wherein the second tip region has an outer diameter and wherein the recessed region intersects the second tip region; and
         a third tip region has an outer diameter, wherein the outer diameter of the second tip region is less than the outer diameter of the third tip region, wherein the third tip region extends distally from the distal end of the needle portion, wherein the second tip region is intermediate the first tip region and the third tip region and wherein the outer diameter of the third tip region is not smaller than the outer diameter of the first tip region; and
      a handle portion that is operably attached to the needle portion, wherein the handle portion comprises a connection port and a vacuum control mechanism that are in communication with a handle bore that extends through the handle portion, wherein the needle bore is in communication with the handle bore and wherein the vacuum control mechanism comprises a vacuum aperture that extends through a surface of the handle portion and is in communication with the handle bore;
   a collection vessel that is capable of receiving aspirated bone fragments and tissue; and tubing that operably connects the connection port and the collection vessel;
   a guide wire that is capable of extending through at least a portion of the needle portion and the handle portion; and
   a gasket provided on the handle portion, wherein the guide wire passes through the gasket when extending through the handle portion.

2. The bone fragment and osteomedullary tissue harvesting system of claim 1, wherein the needle bore intersects the handle bore intermediate the connection port and the vacuum control mechanism.

3. The bone fragment and osteomedullary tissue harvesting system of claim 1, wherein at least part of the needle portion is flexible.

4. The bone fragment and osteomedullary tissue harvesting system of claim 1, wherein the needle portion comprises an inner shaft and an outer shaft and wherein the outer shaft extends over at least a portion of the inner shaft.

5. The bone fragment and osteomedullary tissue harvesting system of claim 4, wherein the inner shaft is fabricated from a metallic material and wherein the outer shaft is fabricated from a polymeric material.

6. The bone fragment and osteomedullary tissue harvesting system of claim 4, wherein the tip portion is attached to the inner shaft.

\* \* \* \* \*